United States Patent [19]
Yonemoto et al.

[11] Patent Number: 6,083,985
[45] Date of Patent: Jul. 4, 2000

[54] MEDICINAL COMPOSITION

[75] Inventors: Mari Yonemoto; Kenji Tanaka; Yoshikazu Iwasawa, all of Tsukuba, Japan

[73] Assignee: Banyu Pharmaceutical Co., Ltd., Tokyo, Japan

[21] Appl. No.: 09/000,495

[22] PCT Filed: Aug. 8, 1996

[86] PCT No.: PCT/JP96/02241
§ 371 Date: Feb. 9, 1998
§ 102(e) Date: Feb. 9, 1998

[87] PCT Pub. No.: WO97/05902
PCT Pub. Date: Feb. 20, 1997

[30] Foreign Application Priority Data

Aug. 9, 1995 [JP] Japan ................................... 7-224659

[51] Int. Cl.⁷ ............................ A61K 31/42; A61K 31/19

[52] U.S. Cl. ............................ 514/568; 514/569; 514/379
[58] Field of Search ..................................... 514/568, 379, 514/569

[56] References Cited

U.S. PATENT DOCUMENTS 5,643,958  7/1997  Iwasawa et al. ......................... 514/568

OTHER PUBLICATIONS

117CA163498s Sumi et al, 1992.

*Primary Examiner*—Russell Travers
*Attorney, Agent, or Firm*—Oblon, Spivak McClelland, Maier & Neustadt, P.C.

[57] ABSTRACT

The present invention relates to an antitumor or anti-AIDS composition containing a protein-farnesyltransferase inhibitor and an agent which decreases farnesyl pyrophosphate in vivo as active ingredients.

20 Claims, No Drawings

MEDICINAL COMPOSITION

This application is a 371 of PCT/JP96/02241 filed Aug. 8, 1996.

TECHNICAL FIELD

The present invention is useful in the medicinal field. In particular, the present invention relates to an antitumor or anti-AIDS composition containing a protein-farnesyltransferase (PFT) inhibitor and an agent which decreases farnesyl pyrophosphate in vivo as active ingredients.

BACKGROUND ART

The ras oncogenes are activated through mutation and their translation products, the Ras proteins, play an important role in transformation of normal cells to cancer cells. Active ras oncogenes are observed in many types of cancer such as colorectal cancer and pancreatic cancer, reportedly in about 25% of human cancers. Accordingly, suppression of activation of the ras oncogenes or inhibition of the function of their products, the Ras protein, leads to prevention of carcinogenesis and is expected to produce an antitumor effect.

On the other hand, it has been revealed recently that the Ras proteins require their farnesylation in order to function and that inhibition of farnesylation prevents the Ras proteins from localizing on cell membranes and thus blocks carcinogenic transformation of cells. The activation of the Ras oncoproteins can be depressed by inhibiting protein-farnesyltransferase (PFT), the enzyme which catalyses farnesylation of the Ras proteins. Since the enzyme is involved in farnesylation of a limited number of proteins in the body, PFT inhibitors are promising as safe and selective antitumor agents. From this standpoint, a number of PFT inhibitors have been developed recently [Cell, vol. 57, 1167–1177 (1989); Proc. Natl. Acad. Sci, vol. 86, 8323–8327 (1989); Proc. Natl. Acad, Sci, vol. 90, 2281–2285 (1993); Science, vol. 245, 379–385 (1989); Science, vol. 260, 1934–1937 (1993); Science, vol. 260, 1937–1942 (1993); J. Biol. Chem., vol. 266, 15575–15578 (1991); J. Antibiotics, vol. 46, 222–227 (1993); Japanese Unexamined Patent Publication JP-A-5-201869; Japanese Unexamined Patent Publication JP-A-5-213992].

Recent study by the present inventors demonstrated that these PFT inhibitors can block the reactivation of static viruses by suppressing development of matured Ras proteins and are useful as anti-AIDS (HIV) agents (Japanese Patent Application JP6-331691).

However, in order to development them as drugs, there still remain problems that most of these PFT inhibitors have low activities in cells and do not have sufficient effect in vivo.

It is reported that agents which decrease farnesyl pyrophosphate in vivo, especially those which inhibit biosynthesis of farnesyl pyrophosphate such as hydroxymethylglutaryl CoA reductase (HMG CoA reductase) inhibitors are expected to exert antitumor effect by suppressing the functioning of the Ras oncoproteins [J. Biol Chem., vol. 265, 19937–19941 (1990)]. However, these agents exhibit quite insufficient antitumor activities when they are used alone.

DISCLOSURE OF INVENTION

The object of the present invention is to provide a novel antitumor or anti-AIDS agent which suppresses the function of, the Ras oncoprotein and thereby exerts antitumor or anti-AIDS effect.

The present inventors have found that compositions containing a protein-farnesyltransferase inhibitor in combination with an agent which decreases farnesyl pyrophosphate in vivo suppresses the function of the Ras oncoproteins remarkably and are useful as antitumor or anti-AIDS agents, and have accomplished the present invention.

The present invention provides an antitumor or anti-AIDS composition containing a protein-farnesyltransferase inhibitor and an agent which decreases farnesyl pyrophosphate in vivo as active ingredients.

The symbols and terms used herein will be explained.

There is no restriction on the agent which decreases farnesyl pyrophosphate in vivo, as long as it is a pharmaceutically acceptable agent having such an action. For example, inhibitors of biosynthesis of farnesyl pyrophosphate are preferred. In particular, agents which inhibit biosynthesis of farnesyl pyrophosphate such as hydroxymethylglutaryl CoA reductase inhibitors like lovastatin, simvastatin, pravastatin and fluvastatin, which are disclosed in Nature, vol. 343, 425–430 (1990) and hydroxymethylglutaryl CoA synthase inhibitors may be mentioned, and particularly preferred are hydroxymethylglutaryl CoA reductase inhibitors such as lovastatin, simvastatin, pravastatin and fluvastatin.

There is no restriction on the protein-farnesyltransferase inhibitor as long as it is a pharmaceutically acceptable agent which inhibits the function of protein-farnesyltransferase in vivo. However, in the present invention, a competitive inhibitor which competes with farnesyl pyrophosphate is preferred, and for example, a compound represented by general formula [I-a]:

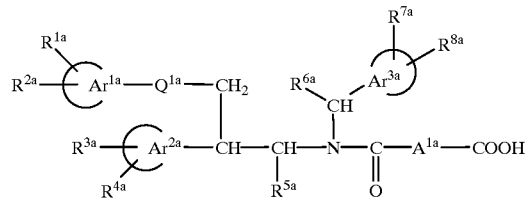

wherein each of

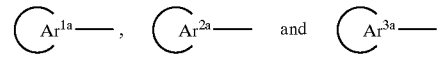

which may be the same or different is an aryl group or an aromatic heterocyclic group; $A^{1a}$ is a saturated or unsaturated aliphatic $C_{2\text{-}8}$ hydrocarbon group which may have substituents from the group consisting of lower alkyl groups, hydroxyl groups, lower hydroxyalkyl groups, lower alkoxy groups, carboxyl groups, lower carboxyalkyl groups, aryl groups and aralkyl groups; $Q^{1a}$ is $-(CH_2)_m-$ (wherein m is an integer of from 1 to 6) or $-(CH_2)_n-W^{1a}-(CH_2)_p-$ (wherein $W^{1a}$ is an oxygen atom, a sulfur atom, a vinylene group or an ethynylene group; each of n and p which may be the same or different is an integer of from 0 to 3); $R^{1a}$ is a hydrogen atom, a halogen atom, a hydroxyl group, a lower alkyl group, a lower alkoxy group or an aryl or aromatic heterocyclic group which may have substituents selected from the group consisting of halogen atoms, lower alkyl groups or lower alkoxy groups; each of $R^{2a}$, $R^{7a}$ and $R^{8a}$ which may be the same or different is a hydrogen atom, a halogen atom, a hydroxyl group, a lower alkyl group or a lower alkoxy group; each of $R^{3a}$ and $R^{4a}$ which may be the same or different is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^{5a}$ is a lower alkyl group; and $R^{6a}$ is a hydrogen atom or a lower alkyl group, or a compound represented by general formula [I-b]:

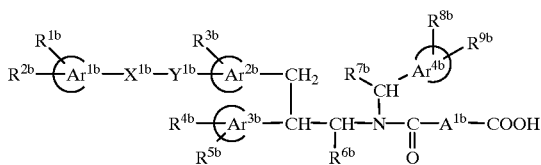

[I-b]

wherein each of

which may be the same or different is an aryl group or an aromatic heterocyclic group; $A^{1b}$ is a saturated or unsaturated aliphatic $C_{2-8}$ hydrocarbon group which may have substituents selected from the group consisting of lower alkyl groups, hydroxyl groups, lower hydroxyalkyl groups, lower alkoxy groups, carboxyl groups, lower carboxyalkyl groups, aryl groups and aralkyl groups; each of $X^{1b}$ and $Y^{1b}$ which may be the same or different is an oxygen atom, a sulfur atom, a carbonyl group, —$CHR^{10b}$— (wherein $R^{10b}$ is a hydrogen atom or a lower alkyl group) or —$NR^{11b}$— (wherein $R^{11b}$ is a hydrogen atom or a lower alkyl group), or $X^{1b}$ and $Y^{1b}$ together represent a vinylene group or an ethynylene group; each of $R^{1b}$, $R^{2b}$, $R^{3b}$, $R^{8b}$ and $R^{9b}$ which may be the same or different is a hydrogen atom, a halogen atom, a hydroxyl group, a lower alkyl group or a lower alkoxy group; each of $R^{4b}$ and $R^{5b}$ which may be the same or different is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^{6b}$ is a lower alkyl group; and $R^{7b}$ is a hydrogen atom or a lower alkyl group, provided that when either $X^{1b}$ or $Y^{1b}$ is an oxygen atom, a sulfur atom or —$NR^{11b}$— (wherein $R^{11b}$ is the same as defined above), the other is a carbonyl group or —$CHR^{10b}$— (wherein $R^{10b}$ is the same as defined above) may be mentioned.

The compounds represented by the general formula [I-a] or [I-b] will be described in detail with reference to the definition of the symbols and terms and preferred embodiments.

The aryl group means a phenyl group, a naphthyl group or an anthryl group, preferably a phenyl group or a naphthyl group.

The aromatic heterocyclic group means a 5- or 6-membered monocyclic aromatic heterocyclic group containing one or two hetero atoms which may be the same or different and are selected from oxygen atoms, nitrogen atoms and sulfur atoms, or a condensed aromatic heterocyclic group composed of such a monocyclic aromatic heterocyclic group condensed with the above-mentioned aryl group or composed of the same or different mononuclear aromatic heterocyclic groups condensed together. For example, a pyrrolyl group, an imidazolyl group, a pyrazolyl group, a pyridyl group, a pyrazinyl group, a pyrimidinyl group, a pyridazinyl group, an oxazolyl group, an isoxazolyl group, a furyl group, a thienyl group, a thiazolyl group, an isothiazolyl group, an indolyl group, a benzofuranyl group, a benzothienyl group, a benzimidazolyl group, benzoxazolyl group, benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group and a pteridinyl group may be mentioned. In particular, a furyl group, a thienyl group, a pyridyl group, a pyrimidinyl group, an oxazolyl group, isoxazolyl group, thiazolyl group, a benzofuranyl group, a benzothienyl group, a benzimidazolyl group, a benzoxazolyl group, a benzothiazolyl group and a quinolyl group are preferred.

The lower alkyl group means a linear or branched alkyl group having from 1 to 6 carbon atoms, such as a methyl group, an ethyl group, a propyl group, an isopropyl group, a butyl group, a sec-butyl group, a tert-butyl group, a pentyl group or a hexyl group, preferably a methyl group or an ethyl group.

The aralkyl group means the above-mentioned lower alkyl group substituted with the above-mentioned aryl group, such as a benzyl group, a phenethyl group, a 3-phenylpropyl group, a 1-naphthylmethyl group, a 2-naphthylmethyl group and a 1-(2-naphthyl)ethyl group, preferably a benzyl group, a phenethyl group or a 2-naphthylmethyl group.

The lower hydroxyalkyl group means the above lower alkyl group having hydroxy group(s), namely a hydroxyalkyl group having from 1 to 6 carbon atoms, such as a hydroxymethyl group, a hydroxyethyl group, a hydroxypropyl group or hydroxybutyl group, preferably a hydroxymethyl group or a hydroxyethyl group.

The lower alkoxy group means an alkoxy or alkylenedioxy group having from 1 to 6 carbon atoms, such as a methoxy group, an ethoxy group, a propoxy group, an isopropoxy group, a butoxy group, a tert-butoxy group, a methylenedioxy group, an ethylenedioxy group or a trimethylenedioxy group, preferably a methoxy group, an ethoxy group or a methylenedioxy group.

The lower carboxyalkyl group means the above lower alkyl group having carboxyl group(s), namely a carboxyalkyl group having from 1 to 7 carbon atoms, such as a carboxymethyl group, a carboxyethyl group, a carboxypropyl group or a carboxybutyl group, preferably a carboxymethyl group or a carboxyethyl group.

As the saturated aliphatic hydrocarbon group, an ethylene group, a trimethylene group, a tetramethylene group, a pentamethylene group, a hexamethylene group, a heptamethylene group or an octamethylene group may be mentioned. Particularly preferred is a trimethylene group, a tetramethylene group or a pentamethylene group.

The unsaturated aliphatic hydrocarbon group means an unsaturated aliphatic hydrocarbon group having one or at least two double bonds, preferably one or two double bonds at optional positions in the carbon chain, such as a vinylene group, a propenylene group, a 1-butenylene group, a 2-butenylene group, a 1,3-butadienylene group, a 1-pentenylene group, a 2-pentenylene group, a 1,3-pentadienylene group, a 1,4-pentadienylene group, a 1-hexenylene group, a 2-hexenylene group, a 3-hexenylene group, a 1,3-hexadienylene group, a 1,4-hexadienylene group, a 1,5-hexadienylene group, a 1,3,5-hexatrienylene group, a 1-heptenylene group, a 2-heptenylene group, 3-heptenylene group, a 1,3-heptadienylene group, a 1,4-heptadienylene group, a 1,5-heptadienylene group, a 1,6-heptadienylene group, a 1,3,5-heptatrienylene group, a 1-octenylene group, a 2-octenylene group, a 3-octenylene group, 4-octenylene, a 1,3-octadienylene group, a 1,4-octadienylene group, a 1,5-octadienylene group, a 1,6-octadienylene group, a 1,7-octadienylene group, a 2,4-octadienylene group, a 2,5-octadienylene group, a 2,6-octadienylene group, a 3,5-octadienylene group, 1,3,5-octatrienylene group, a 2,4,6-octatrienylene group or a 1,3, 5,7-octatetraenylene group, preferably a propenylene group, a 1-butenylene group, 1,3-butadienylene group or a 1-pentenylene group.

The halogen atom means a fluorine atom, a chlorine atom, a bromine atom or an iodine atom, preferably a fluorine atom or a chlorine atom.

The lower alkoxycarbonyl group means an alkoxycarbonyl group having from 1 to 7 carbon atoms, such as a methoxycarbonyl group, an ethoxycarbonyl group, a propoxycarbonyl group, a butoxycarbonyl group or a tert-butoxycarbonyl group, preferably a methoxycarbonyl group or an ethoxycarbonyl group.

The lower alkylcarbamoyl group means a carbamoyl group substituted with the above one or two lower alkyl groups, such as a methylcarbamoyl group, an ethylcarbamoyl group, a dimethylcarbamoyl group or a diethylcarbamoyl group.

The lower fluoroalkyl group means the above lower alkyl group having fluorine atom(s), namely a fluoroalkyl group having from 1 to 6 carbon atoms, such as a fluoromethyl group, a difluoromethyl group, a trifluoromethyl group, a 1-fluoroethyl group, a 2-fluoroethyl group, a 2,2,2-trifluoroethyl group or a pentafluoroethyl group.

The salt of the compound of the formula [I-a] or [I-b] means a common pharmaceutically acceptable salt and may, for example, be a base addition salt of the carboxyl group, or an acid addition salt of the basic nitrogen.

The base addition salt may, for example, be an alkali metal salt such as a sodium salt or a potassium salt; an alkaline earth metal salt such as a calcium salt or a magnesium salt; an ammonium salt; an organic amine salt such as a trimethylamine salt, a triethylamine salt, a dicyclohexylamine salt, an ethanolamine salt, a diethanolamine salt, a triethanolamine salt, a procaine salt or a N,N'-dibenzylethylenediamine salt.

The acid addition salt may, for example, be an inorganic acid salt such as a hydrochloride, a sulfate, a nitrate, a phosphate or a perchlorate; an organic acid salt such as a maleate, a fumarate, a tartrate, a citrate, an ascorbate or a trifluoroacetate; or a sulfonate such as a methanesulfonate, an isethionate, a benzenesulfonate or a p-toluenesulfonate.

The ester of the compound of formula [I-a] or [I-b] means a common pharmaceutically acceptable ester, and may, for example, be an ester with a lower alkyl group such as a methyl group, an ethyl group, a propyl group, an isopropyl group, a butyl group, a sec-butyl group, a tert-butyl group, a cyclopropyl group or a cyclopentyl group, an ester with an aralkyl group such as a benzyl group or a phenethyl group, an ester with a lower alkenyl group such as an allyl group or a 2-butenyl group, an ester with a lower alkoxyalkyl group such as a methoxymethyl group, a 2-methoxyethyl group or a 2-ethoxyethyl group, an ester with a lower alkanoyloxyalkyl group such as an acetoxymethyl group, a pivaloyloxymethyl group or a 1-pivaloyloxyethyl group, an ester with a lower alkoxycarbonylalkyl group such as a methoxycarbonylmethyl group or an isopropoxycarbonylmethyl group, an ester with a lower carboxyalkyl group such as a carboxymethyl group, an ester with a lower alkoxycarbonyloxyalkyl group such as a 1-(ethoxycarbonyloxy)ethyl group or a 1-(cyclohexyloxycarbonyloxy)ethyl group, an ester with a lower carbamoyloxyalkyl group such as a carbamoyloxymethyl group, an ester with a phthalidyl group or an ester with a (5-substituted-2-oxo-1,3-dioxol-4-yl) methyl group such as a (5-methyl-2-oxo-1,3-dioxol-4-yl) methyl group.

Further, when a hydroxyl group is present at the γ- or δ-position of the terminal carboxyl group or of a carboxyl group when such a carboxyl group or a lower carboxyalkyl group is present on the saturated or unsaturated aliphatic hydrocarbon group represented by A in the formula, such a hydroxyl group and a carboxyl group may form an intramolecular ester, namely, a 5- or 6-membered lactone ring.

The compound represented by general formula [I-a] or [I-b] may have stereoisomers such as optical isomers, diastereomers and geometrical isomers, depending upon the form of its substituents. The present invention includes all these stereoisomers and their mixtures. In particular, a compound represented by general formula [I'-a-1]:

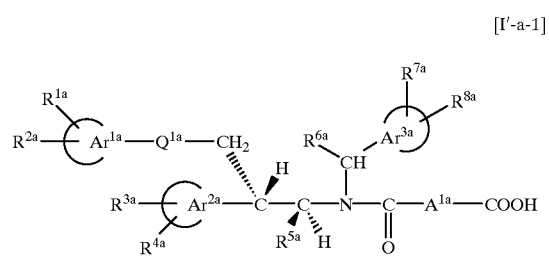

[I'-a-1]

or by general formula [I'-a-2]:

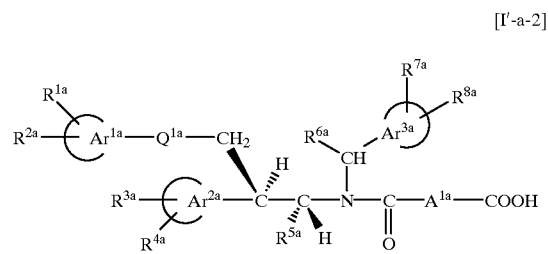

[I'-a-2]

wherein $Ar^{1a}$—, $Ar^{2a}$—, $Ar^{3a}$—, $A^{1a}$, $Q^{1a}$, $R^{1a}$, $R^{2a}$, $R^{3a}$, $R^{4a}$, $R^{5a}$, $R^{6a}$, $R^{7a}$ and $R^{8a}$ are the same as defined above, or a compound represented by general formula [I'-b-1]:

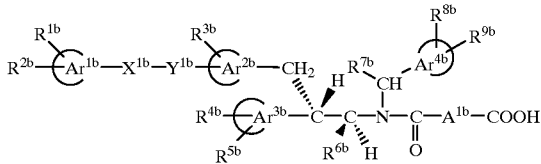

[I'-b-1]

or by general formula [I'-b-2]:

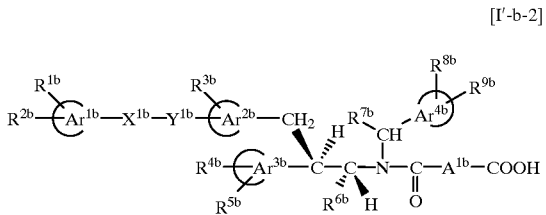

[I'-b-2]

wherein

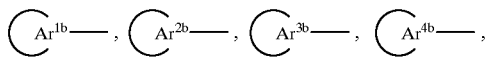

$A^{1b}, X^{1b}, Y^{1b}, R^{1b}, R^{2b}, R^{3b}, R^{4b}, R^{5b}, R^{6b}, R^{7b}, R^{8b}$ and $R^{9b}$ are the same as defined above is preferred.

When $W^{1a}$ is a vinylene group, the group —$(CH_2)_n$—$W^{1a}$—$(CH_2)_p$— (wherein $W^{1a}$, n and p are the same as defined above) as $Q^{1a}$ has geometric isomers, the E isomer (the trans-isomer) and the Z isomer (the cis-isomer), in relation to the vinylene group. In such a case, the E isomer is preferred.

In general formula [1-b], each of $X^{1b}$ and $Y^{1b}$ which may be the same or different, is an oxygen atom, a sulfur atom, a carbonyl group, —$CHR^{10b}$— (wherein $R^{10b}$ is a hydrogen atom or a lower alkyl group) or —$NR^{11b}$— (wherein $R^{11b}$ is a hydrogen atom or a lower alkyl group), or $X^{1b}$ and $R^{1b}$ together represent a vinylene group or an ethynylene group, provided that when either $X^{1b}$ or $Y^{1b}$ is an oxygen atom, a sulfur atom or —$NR^{11b}$— (wherein $R^{11b}$ is the same as defined above), the other is a carbonyl group or a —$CHR^{10b}$— (wherein $R^{10b}$ is the same as defined above).

As the compound represented by general formula [I-b], a compound wherein $X^{1b}$ is —$NR^{11b}$— (wherein $R^{11b}$ is the same as defined above), and $Y^{1b}$ is a carbonyl group, a compound wherein $X^{1b}$ is an oxygen atom, and $Y^{1b}$ is —$CHR^{10b}$— (wherein $R^{10b}$ is the same as defined above) or a compound wherein both $X^{1b}$ and $Y^{1b}$ are —$CHR^{10b}$— (wherein $R^{10b}$ is the same as defined above) is preferred.

In general formula [I-a] or [I-b], the saturated or unsaturated aliphatic $C_{2-8}$ hydrocarbon group, as $A^{1a}$ or $A^{1b}$, which may have substituents selected from the group consisting of lower alkyl groups, hydroxyl groups, lower hydroxyalkyl groups, lower alkoxy groups, carboxyl groups, lower carboxyalkyl groups, aryl groups and aralkyl groups, means the above-mentioned saturated or an unsaturated aliphatic hydrocarbon group which is not substituted or the above-mentioned saturated or unsaturated aliphatic hydrocarbon group having one or at least two identical or different substituents, preferably from 1 to 3 identical or different substituents selected from the group consisting of lower alkyl groups, hydroxyl groups, lower hydroxyalkyl groups, lower alkoxy groups, carboxyl groups, lower carboxyalkyl groups, aryl groups and aralkyl groups, at optional substitutable positions.

A compound wherein $A^{1a}$ or $A^{1b}$ is a group represented by formula [a]:

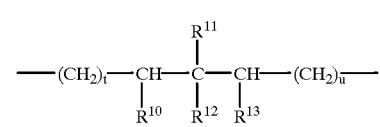

[a]

(wherein $R^{10}$ is a hydrogen atom, a hydroxyl group, a lower hydroxyalkyl group, a lower alkoxy group or a carboxyl group; $R^{11}$ is a hydrogen atom, a hydroxyl group, a lower alkoxy group, a carboxyl group or a lower carboxyalkyl group; $R^{12}$ is a hydrogen atom, a lower hydroxyalkyl group or a carboxyl group; $R^{13}$ is a hydrogen atom, a hydroxyl group or a carboxyl group; and each of t and u which may be the same or different is an integer of from 0 to 2) and a compound wherein $A^{1a}$ or $A^{1b}$ is a group represented by formula [b]:

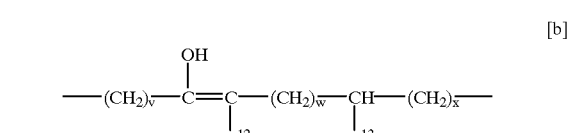

[b]

(wherein $R^{12}$ is a hydrogen atom, a lower hydroxyalkyl group or a carboxyl group; $R^{13}$ is a hydrogen atom, a hydroxyl group or a carboxyl group; v is 0 or 1; and each of w and x which may be the same or different is an integer of from 0 to 2) are preferred.

When $A^{1a}$ or $A^{1b}$ is represented by [a], $R^{10}$ is preferably a hydrogen atom, a hydroxyl group or a carboxyl group, $R^{11}$ is preferably a carboxyl group or a lower carboxyalkyl group such as a carboxymethyl group, each of $R^{12}$ and $R^{13}$ is preferably a hydrogen atom or a carboxyl group, and each of t and u which may be the same or different is preferably 0 or 1.

When $A^{1a}$ or $A^{1b}$ is represented by formula [b], $R^{12}$ is preferably a lower hydroxyalkyl group such as a hydroxymethyl group or a carboxyl group, $R^{13}$ is preferably a hydrogen atom, and each of v, w and x is preferably 0.

In general formula [I-a], when $Q^{1a}$ is —$(CH_2)_m$— (wherein m is the same as defined above), m is preferably from 1 to 4, and when $Q^{1a}$ is —$(CH_2)_n$—$W^{1a}$—$(CH_2)_p$— (wherein $W^{1a}$, n and p are the same as defined above), $W^{1a}$ is preferably a vinylene group or an ethynylene group, more preferably a vinylene group, and each of n and p which may be the same or different is preferably 0 or 1.

With respect to

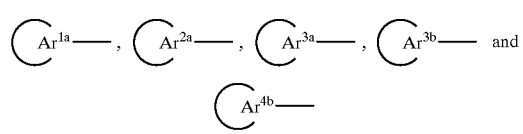

in the compound represented by general formula [I-a] or [I-b],

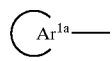

is preferably a phenyl group, a naphthyl group, a benzofuranyl group, a benzothienyl group or a benzoxazolyl group,

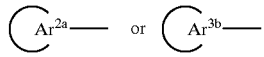

is preferably a phenyl group, and

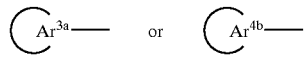

is preferably a naphthyl group, a benzofuranyl group or a benzothienyl group.

In general formula [I-a], the aryl or aromatic heterocyclic group which may have substituents selected from the group consisting of halogen atoms, lower alkyl groups and lower alkoxy groups as $R^{1a}$ means the above-mentioned aryl or aromatic heterocyclic group which is not substituted, or the above-mentioned aryl or aromatic heterocyclic group which has one or at least two identical or different substituents selected from the group consisting of halogen atoms, lower alkyl group and lower alkoxy groups, at optional substitutable positions. In particular, the above-mentioned unsubstituted aryl or aromatic heterocyclic group is preferred.

In the compound represented by general formula [I-a], the group represented by the formula:

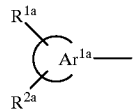

may, for example, be

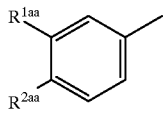

(wherein $R^{1aa}$ is a hydrogen atom, a halogen atom, a lower alkyl group or a lower alkoxy group; and $R^{2aa}$ is a hydrogen atom, a halogen atom or a lower alkyl group), a naphthyl group, a benzofuranyl group, a benzothienyl group, a benzothiazolyl group, a benzoxazolyl group or a benzimidazolyl group, and is preferably a phenyl group, a 2-benzo[b]furanyl group, a 2-benzo[b]thienyl group, a 2-naphthyl group or a 2-benzoxazolyl group.

The group represented by the formula

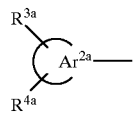

may, for example, be

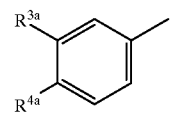

(wherein $R^{3a}$ and $R^{4a}$ are the same as defined above), a naphthyl group or a pyridyl, furyl or thienyl group having $R^{3a}$ on the ring, and is preferably a 4-fluorophenyl group, a 4-chlorophenyl group, a 4-methylphenyl group, a 3-fluoro-4-methylphenyl group, a 4-fluoro-3-methylphenyl group, a 3-chloro-4-methylphenyl group, a 4-chloro-3-methylphenyl group, a 3,4-dichlorophenyl group, a 3,4-dimethylphenyl group, a 4-methoxyphenyl group, a 3,4-dimethoxyphenyl group, a 4-nitrophenyl group, a 4-aminophenyl group, a 4-hydroxyphenyl group, a 4-carbamoylphenyl group, a 4-methylcarbamoylphenyl group, a 4-hydroxymethylphenyl group, a 4-trifluoromethylphenyl group, a 4-cyanophenyl group, a 4-methoxycarbonylphenyl group, a 3,4-methylenedioxyphenyl group, a 4-hydroxy-3-methoxyphenyl group, a 3-hydroxy-4-methoxyphenyl group, a 3,4-bis(methoxycarbonyl)phenyl group, a 3,4-bis(hydroxymethyl)phenyl group, a 1-naphthyl group, a 2-naphthyl group, a 5-methylfuryl group, a 5-methylthienyl group or a 6-methyl-3-pyridyl group.

$R^{5a}$ or $R^{6b}$ is preferably a methyl group, an ethyl group or a propyl group, more preferably a methyl group or an ethyl group.

$R^{6a}$ or $R^{7a}$ is preferably a hydrogen atom, a methyl group, an ethyl group or a propyl group, more preferably a hydrogen atom or a methyl group.

The group represented by

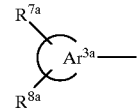

may, for example, be

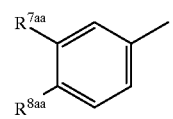

(wherein each of $R^{7aa}$ and $R^{8aa}$ which may be the same or different is a hydrogen atom, a halogen atom, a lower alkyl group or a lower alkoxy group), a naphthyl group, a quinolyl group, a benzoxazolyl group, a benzofuranyl group or a benzothienyl group, preferably a 3,4-dichlorophenyl group, a 3,4-difluorophenyl group, a 3,4-dimethylphenyl group, a 2-naphthyl group, a 2-benzoxazoly group, a 2-benzo[b]furanyl group, a 2-benzo[b]thienyl group or a 5-benzo[b]thienyl group.

Specific examples of the compound represented by general formula [I-a] or [I-b] are, for example:

N-{(1RS,2RS,4E)-2-(4-chlorophenyl)-1-methyl-5-(2-naphthyl)-4-pentenyl}-N-(2-naphthylmethyl)carbamoylmethylsuccinic acid, N-{(1RS,2RS,4E)-2-(4-chlorophenyl)-1-methyl-5-(1-naphthyl)-4-pentenyl}-N-(2-naphthylmethyl)carbamoylmethylsuccinic acid, N-{(1RS,2RS)-2-(4-chlorophenyl)-1-methyl-5-(2-naphthyl)pentyl}-N-(2-naphthylmethyl)carbamoylmethylsuccinic acid, N-{(1RS,2RS)-2-(4-chlorophenyl)-1-methyl-4-(2-naphthoxy)butyl}-N-(2-naphthylmethyl)carbamoylmethylsuccinic acid, N-{(1RS,2RS)-2-(4-chlorophenyl)-1-methyl-4-(2-naphthyl)butyl}-N-(2-naphthylmethyl)carbamoylmethylsuccinic acid, N-{(1RS,2RS)-2-(4-chlorophenyl)-1-methyl-6-(2-naphthyl)hexyl}-N-(2-naphthylmethyl)carbamoylmethylsuccinic acid, N-{(1RS,2RS)-2-(4-chlorophenyl)-1-methyl-5-phenyl-4-pentynyl}-N-(2-naphthylmethyl)carbamoylmethylsuccinic acid, N-{(1RS,2RS,4E)-2-(4-methoxyphenyl)-1-methyl-5-(2-naphthyl)-4-pentenyl}-N-(2-naphthylmethyl)carbamoylmethylsuccinic acid, N-{(1RS,2RS,4E)-1-methyl-2-(4-methylphenyl)-5-(2-naphthyl)-4-pentenyl}-N-(2-naphthylmethyl)carbamoylmethylsuccinic acid, N-{(1RS,2RS,4E)-1-methyl-5-(2-naphthyl)-2-(4-nitrophenyl)-4-pentenyl}-N-(2-naphthylmethyl)carbamoylmethylsuccinic acid, N-{(1RS,2RS,4E)-2-(4-fluorophenyl)-1-methyl-5-(2-naphthyl)-4-pentenyl}-N-(2-naphthylmethyl)carbamoylmethylsuccinic acid, N-{(1RS,2RS,4E)-1-methyl-5-(2-naphthyl)-2-(4-trifluoromethylphenyl)-4-pentenyl}-N-(2-naphthylmethyl)carbamoylmethylsuccinic acid, N-{(1RS,2RS,4E)-1-methyl-5-(2-naphthyl)-2-phenyl-4-pentenyl}-N-(2-naphthylmethyl)carbamoylmethylsuccinic acid, N-{(1RS,2RS,4E)-1-methyl-2-(6-methyl-3-pyridyl)-5-(2-naphthyl)-4-pentenyl}-N-(2-naphthylmethyl)carbamoylmethylsuccinic acid, N-{(1RS,2RS,6E)-2-(4-chlorophenyl)-1-methyl-7-phenyl-6-heptenyl}-N-(2-naphthylmethyl)carbamoylmethylsuccinic acid, N-{(1RS,2RS,6E)-2-(4-chlorophenyl)-1-methyl-7-(2-naphthyl)-6-heptenyl}-N-(2-naphthylmethyl)carbamoylmethylsuccinic acid, N-{(1RS,2RS,4E)-2-(4-chlorophenyl)-1-methyl-5-(2-naphthyl)-4-pentenyl}-N-(3-quinolylmethyl)carbamoylmethylsuccinic acid, N-{(1RS,2RS,4E)-2-(4-chlorophenyl)-1-methyl-5-(2-naphthyl)-4-pentenyl}-N-(3,4-difluorobenzyl)carbamoylmethylsuccinic acid, N-(2-benzoxazolylmethyl)-N-{(1RS,2RS,4E)-2-(4-chlorophenyl)-1-methyl-5-(2-naphthyl)-4-pentenyl}carbamoylmethylsuccinic acid, N-(2-benzo[b]thienylmethyl)-N-{(1RS,2RS,4E)-2-(4-chlorophenyl)-1-methyl-5-(2-naphthyl)-4-pentenyl}carbamoylmethylsuccinic acid, N-{(1RS,2RS,4E)-1-methyl-2-(3,4-methylenedioxyphenyl)-5-(2-naphthyl)-4-pentenyl}-N-(2-naphthylmethyl)carbamoylmethylsuccinic acid, (2R*)-2-[N-{(1S*,2S*,4E)-2-(4-chlorophenyl)-1-methyl-5-(2-naphthyl)-4-pentenyl}-N-(2-naphthylmethyl)carbamoylmethyl]succinic acid, (2R*)-2-[N-{(1R*,2R*,4E)-2-(4-chlorophenyl)-1-methyl-5-(2-naphthyl)-4-pentenyl}-N-(2-naphthylmethyl)carbamoylmethyl]succinic acid, (2S*)-2-[N-{(1R*,2R*,4E)-2-(4-chlorophenyl)-1-methyl-5-(2-naphthyl)-4-pentenyl}-N-(2-naphthylmethyl)carbamoylmethyl]succinic acid, (2S*)-2-[N-{(1S*,2S*,4E)-2-(4-chlorophenyl)-1-methyl-5-(2-naphthyl)-4-pentenyl}-N-(2-naphthylmethyl)carbamoylmethyl]succinic acid, 5-[N-{(1RS,2RS,4E)-2-(4-chlorophenyl)-1-methyl-5-(2-naphthyl)-4-pentenyl}-N-(2-naphthylmethyl)carbamoyl]pentanoic acid, (2R*)-2-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]succinic acid, (2R*)-2-[N-{(1RS,2RS,4Z)-5-(2-benzoxazolyl)-1-methyl-2-(3,4-methylenedioxyphenyl)-4-pentenyl}-N-(2-naphthylmethyl)carbamoylmethyl]succinic acid, (2R*)-2-[N-(2-benzo[b]furanylmethyl)-N-{(1RS,2RS,4E)-5-(2-benzoxazolyl)-1-methyl-2-(3,4-methylenedioxyphenyl)-4-pentenyl}carbamoylmethyl]succinic acid, (2R*)-2-[N-(2-benzo[b]thienylmethyl)-N-{(1RS,2RS,4E)-5-(2-benzoxazolyl)-1-methyl-2-(3,4-methylenedioxyphenyl)-4-pentenyl}carbamoylmethyl]succinic acid, (2R*)-2-[N-{(1RS,2RS,4E)-5-(2-benzoxazolyl)-2-{3,4-bis(methoxycarbonyl)phenyl}-1-methyl-4-pentenyl}-N-(2-naphthylmethyl)carbamoylmethyl]succinic acid, (2R*)-2-[N-(2-benzo[b]thienylmethyl)-N-{(1RS,2RS,4E)-5-(2-benzoxazolyl)-2-(4-methoxycarbonylphenyl)-1-methyl-4-pentenyl}carbamoylmethyl]succinic acid, (2R*)-2-[N-(2-benzo[b]furanylmethyl)-N-{(1RS,2RS,4E)-5-(2-benzoxazolyl)-2-(4-methoxycarbonylphenyl)-1-methyl-4-pentenyl}carbamoylmethyl]succinic acid, (2R*)-2-[N-(2-benzo[b]thienylmethyl)-N-{(1RS,2RS,4E)-5-(2-benzoxazolyl)-2-(4-cyanophenyl)-1-methyl-4-pentenyl}carbamoylmethyl]succinic acid, (2R*)-2-[N-(5-benzo[b]thienylmethyl)-N-{(1RS,2RS,4E)-5-(2-benzoxazolyl)-2-(4-methoxycarbonylphenyl)-1-methyl-4-pentenyl}carbamoylmethyl]succinic acid, N-{(1RS,2RS,4E)-5-(3-chloro-4-methylphenyl)-2-(4-chlorophenyl)-1-methyl-4-pentenyl}-N-(2-naphthylmethyl)carbamoylmethylsuccinic acid, N-{(1RS,2RS,4Z)-5-(3-chloro-4-methylphenyl)-2-(4-chlorophenyl)-1-methyl-4-pentenyl}-N-(2-naphthylmethyl)carbamoylmethylsuccinic acid, N-{(1RS,2RS,4E)-5-(2-benzo[b]furanyl)-2-(4-chlorophenyl)-1-methyl-4-pentenyl}-N-(2-naphthylmethyl)carbamoylmethylsuccinic acid, N-{(1RS,2RS,4Z)-5-(2-benzo[b]furanyl)-2-(4-chlorophenyl)-1-methyl-4-pentenyl}-N-(2-naphthylmethyl)carbamoylmethylsuccinic acid, N-{(1RS,2RS,4E)-5-(2-benzoxazolyl)-2-(4-chlorophenyl)-1-methyl-4-pentenyl}-N-(2-naphthylmethyl)carbamoylmethylsuccinic acid, N-{(1RS,2RS,4Z)-5-(2-benzoxazolyl)-2-(4-chlorophenyl)-1-methyl-4-pentenyl}-N-(2-naphthylmethyl)carbamoylmethylsuccinic acid, N-{(1RS,2RS,4E)-5-(2-benzimidazolyl)-2-(4-chlorophenyl)-1-methyl-4-pentenyl}-N-(2-naphthylmethyl)carbamoylmethylsuccinic acid, N-{(1RS,2RS,4E)-2-(4-chlorophenyl)-1-methyl-5-(3,4-methylenedioxyphenyl)-4-pentenyl}-N-(2-naphthylmethyl)carbamoylmethylsuccinic acid, N-{(1RS,2RS,4E)-5-(2-benzothiazolyl)-2-(4-chlorophenyl)-1-methyl-4-pentenyl}-N-(2-naphthylmethyl)carbamoylmethylsuccinic acid, N-{(1RS,2RS,4E)-5-(2-benzoxazolyl)-2-(4-cyanophenyl)-1-methyl-4-pentenyl}-N-(2-naphthylmethyl)carbamoylmethylsuccinic acid, 4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-1,2,3-butanetricarboxylic acid, 3-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-1,2,2-propanetricarboxylic acid, (2S,3R)-4-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]-3-carboxy-2-hydroxybutanoic acid, 4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-3-carboxy-4-methoxybutanoic acid, 5-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-4-carboxy-3-carboxymethylpentanoic acid, 1-[N-{(1RS,2RS,4E)-5-(2-benzoxazolyl)-2-(4-methoxycarbonylphenyl)-1-methyl-4-pentenyl}-N-(2-naphthylmethyl)carbamoyl]-1,2,3-propanetricarboxylic acid, (3R*)-4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-3-methoxybutanoic acid, (3S*)-4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-3-methoxybutanoic acid, N-{(1RS,2RS,4E)-5-(2-benzoxazolyl)-2-(4-carboxyphenyl)-1-methyl-4-pentenyl}-N-(2-naphthylmethyl)carbamoylmethylsuccinic acid, N-[(1RS,2RS,4E)-5-(2-benzoxazolyl)-1-methyl-2-{4-(N-methylcarbamoyl)phenyl}-4-pentenyl]-N-(2-naphthylmethyl)carbamoylmethylsuccinic acid, (2R*)-2-[N-{(1RS,2RS,4E)-5-(2-benzoxazolyl)-2-(4-hydroxy-3-methoxyphenyl)-1-methyl-4-pentenyl}-N-(2-naphthylmethyl)carbamoylmethyl]succinic acid, N-{(1RS,2RS,4E)-2-(4-hydroxymethylphenyl)-1-methyl-5-(2-naphthyl)-4-pentenyl}-N-(2-naphthylmethyl)carbamoylmethylsuccinic acid, N-{(1RS,2RS,4E)-2-(4-aminophenyl)-1-methyl-5-(2-naphthyl)-4-pentenyl}-N-(2-naphthylmethyl)carbamoylmethylsuccinic acid, Disodium (3RS,4RS)-4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-3-carboxylato-4-hydroxybutanoate, N-{(1RS,2RS,4E)-5-(2-benzoxazolyl)-1-methyl-2-(3,4-methylenedioxyphenyl)-4-pentenyl}-N-(2-naphthylmethyl)-5-oxotetrahydrofuran-2-carboxamide, Sodium 4-[N-{(1RS,2RS,4E)-5-(2-benzoxazolyl)-1-methyl-2-(3,4-methylenedioxyphenyl)-4-pentenyl}-N-(2-naphthylmethyl)]carbamoyl-4-hydroxybutanoate, 4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-2-oxotetrahydrofuran-3-ylacetic acid, (2R*)-2-[N-{(1R*,2R*,4E)-5-(2-benzoxazolyl)-2-(4-methoxycarbonylphenyl)-1-methyl-4-pentenyl}-N-(2-naphthylmethyl)carbamoylmethyl]succinic acid, (2R*)-2-[N-{(1S*,2S*,4E)-5-(2-benzoxazolyl)-2-(4-methoxycarbonylphenyl)-1-methyl-4-pentenyl}-N-(2-naphthylmethyl)carbamoylmethyl]succinic acid, (2R*)-2-[N-(2-benzo[b]thienylmethyl)-N-{(1S*,2S*,4E)-5-(2-benzoxazolyl)-1-methyl-2-(3,4-methylenedioxyphenyl)-4-pentenyl}carbamoylmethyl]succinic acid, (2R*)-2-[N-(2-benzo[b]thienylmethyl)-N-{(1R*,2R*,4E)-5-(2-benzoxazolyl)-1-methyl-2-(3,4-methylenedioxyphenyl)-4-pentenyl}carbamoylmethyl]succinic acid, (2R*)-2-[N-{(1RS,2RS)-5-(2-benzoxazolyl)-1-methyl-2-(3,4-methylenedioxyphenyl)pentyl}-N-(2-naphthylmethyl)carbamoylmethyl]succinic acid, (2R*)-2-[N-(2-benzo[b]thienylmethyl)-N-{(1RS,2RS)-5-(2-benzoxazolyl)-1-methyl-2-(3,4-methylenedioxyphenyl)pentyl}carbamoylmethyl]succinic acid, (2R*)-2-[N-{(1R*,2R*)-5-(2-benzoxazolyl)-2-(4-methoxycarbonylphenyl)-1-methylpentyl}-N-(2-naphthylmethyl)carbamoylmethyl]succinic acid, Disodium (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-carboxylato-4-hydroxybutanoate, Sodium (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-ethoxycarbonyl-4-hydroxybutanoate, 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxy-3-butenoic acid, 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-methoxycarbonyl-3-butenoic acid, 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-isopropoxycarbonyl-3-butenoic acid, 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-cyclohexyloxycarbonyl-4-hydroxy-3-butenoic acid, 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-(2-methoxyethoxy)carbonyl-3-butenoic acid, 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-benzyloxycarbonyl-4-hydroxy-3-butenoic acid, 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-cyclopentyloxycarbonyl-4-hydroxy-3-butenoic acid, 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-(3-tetrahydrofuranyloxycarbonyl)-3-butenoic acid, 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-(2-hydroxy-1-hydroxymethylethoxycarbonyl)-3-butenoic acid, 3-allyloxycarbonyl-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-butenoic acid, 4-[N-{(1R,2R,4E)-5-(2-benzoxazolyl)-2-(3,4-methylenedioxyphenyl)-1-methyl-4-pentenyl}-N-(2-naphthylmethyl)carbamoyl]-3-carboxymethylcarbonyl-4-hydroxy-3-butenoic acid, 5-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-ethoxycarbonyl-5-hydroxy-4-pentenoic acid, 5-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-tert-butoxycarbonyl-5-hydroxy-4-pentenoic acid, 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-4-hydroxy-3-hydroxymethyl-3-butenoic acid, 4-[N-{(1RS,2RS,5E)-6-(2-benzoxazolyl)-1-methyl-2-(3,4-methylenedioxyphenyl)-5-hexenyl}-N-(2-naphthylmethyl)carbamoyl]-3-tert-butoxycarbonyl-4-hydroxy-3-butenoic acid, (2S*,3R*)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-1,2,3-butanetricarboxylic acid, (2R*,3S*)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-1,2,3-butanetricarboxylic acid, N-[(1RS,2RS)-1-methyl-2-(4-nitrophenyl)-3-{5-(phenylcarbamoyl)-2-furyl}propyl]-N-(2-naphthylmethyl)carbamoylmethylsuccinic acid, N-[(1RS,2RS)-3-{5-(3,4-dimethoxyphenylcarbamoyl)-2-furyl}-1-methyl-2-(4-nitrophenyl)propyl]-N-(2-naphthylmethyl)carbamoylmethylsuccinic acid, N-[(1RS,2RS)-3-{5-(2-hydroxyphenylcarbamoyl)-2-furyl}-1-methyl-2-(4-nitrophenyl)propyl]-N-(2-naphthylmethyl)carbamoylmethylsuccinic acid, N-[(1RS,2RS)-1-methyl-3-{5-(N-methylphenylcarbamoyl)-2-furyl}-2-(4-nitrophenyl)propyl]-N-(2-naphthylmethyl)carbamoylmethylsuccinic acid, N-[(1RS,2RS)-1-methyl-2-(4-nitrophenyl)-3-{5-(3-pyridylcarbamoyl)-2-furyl}propyl]-N-(2-naphthylmethyl)carbamoylmethylsuccinic acid hydrochloride, N-[(1RS,2RS)-1-methyl-2-(4-nitrophenyl)-3-{5-(4-pyridylcarbamoyl)-2-furyl}propyl]-N-(2-naphthylmethyl)carbamoylmethylsuccinic acid hydrochloride, N-[(1RS,2RS)-1-methyl-2-(4-nitrophenyl)-3-{5-(5-pyrimidinylcarbamoyl)-2-furyl}propyl]-N-(2-naphthylmethyl)carbamoylmethylsuccinic acid hydrochloride, N-[(1RS,2RS)-1-methyl-2-(4-nitrophenyl)-3-{5-(2-thiazolylcarbamoyl)-2-furyl}propyl]-N-(2-naphthylmethyl)carbamoylmethylsuccinic acid hydrochloride, N-[(1RS,2RS)-2-(4-chlorophenyl)-1-methyl-3-{5-(phenylcarbamoyl)-2-furyl}propyl]-N-(2-naphthylmethyl)carbamoylmethylsuccinic acid, N-{(1RS,2RS)-2-(4-chlorophenyl)-1-methyl-3-(3-phenylcarbamoylphenyl)propyl}-N-(2-naphthylmethyl)carbamoylmethylsuccinic acid, N-[(1RS,2RS)-2-(4-chlorophenyl)-1-methyl-3-{3-(phenylcarbamoyl)-5-isoxazolyl}propyl]-N-(2-naphthylmethyl)carbamoylmethylsuccinic acid, N-[(1RS,2RS)-2-(4-chlorophenyl)-1-methyl-3-{4-(phenylcarbamoyl)-2-pyridyl}propyl]-N-(2-naphthylmethyl)carbamoylmethylsuccinic acid, (2R*)-2-[N-(2-benzo[b]thienylmethyl)-N-[(1RS,2RS)-1-methyl-2-(3,4-methylenedioxyphenyl)-3-{5-(phenylcarbamoyl)-2-furyl}propyl]carbamoylmethyl]succinic acid, (2R*)-2-[N-(2-benzo[b]thienylmethyl)-N-[(1RS,2RS)-1-methyl-2-(3,4-methylenedioxyphenyl)-3-{5-(3-pyridylcarbamoyl)-2-furyl}propyl]carbamoylmethyl]succinic acid hydrochloride, monopivaloyloxymethyl (2R*)-2-[N-(2-benzo[b]thienylmethyl)-N-[(1RS,2RS)-1-methyl-2-(3,4-methylenedioxyphenyl)-3-{5-(phenylcarbamoyl)-2-furyl}propyl]carbamoylmethyl]succinate, (2R*)-2-[N-{(1RS,2RS)-2-(4-methoxycarbonylphenyl)-1-methyl-3-(3-phenoxymethylphenyl)propyl}-N-(2-naphthylmethyl)carbamoylmethyl]succinic acid, (2R*)-2-[N-[(1RS,2RS)-2-(4-methoxycarbonylphenyl)-1-methyl-3-{3-(phenoxymethyl)-5-(1,2,4-oxadiazolyl)}propyl]-N-(2-naphthylmethyl)carbamoylmethyl]succinic acid, (2R*)-2-[N-[(1RS,2RS)-2-(4-methoxycarbonylphenyl)-1-methyl-3-{(E)-3-styrylphenyl}propyl]-N-(2-naphthylmethyl)carbamoylmethyl]succinic acid, (2R*)-2-[N-[(1RS,2RS)-2-(4-methoxycarbonylphenyl)-1-methyl-3-{3-(2-phenylethyl)phenyl}propyl]-N-(2-naphthylmethyl)carbamoylmethyl]succinic acid, N-{(1RS,2RS)-2-(4-chlorophenyl)-1-methyl-3-(4-phenylethynylphenyl)propyl}-N-(2-naphthylmethyl)carbamoylmethylsuccinic acid, N-[(1RS,2RS)-2-(4-chlorophenyl)-1-methyl-3-{(E)-3-styrylphenyl}propyl]-N-(2-naphthylmethyl)carbamoylmethylsuccinic acid, N-{(1RS,2RS)-2-(4-methoxycarbonylphenyl)-1-methyl-3-(5-phenoxymethyl-2-furyl)propyl}-N-(2-naphthylmethyl)carbamoylmethylsuccinic acid, 4-[N-[(1RS,2RS)-1-methyl-2-(4-nitrophenyl)-3-{5-(phenylcarbamoyl)-2-furyl}propyl]-N-(2-naphthylmethyl)carbamoyl]-1,2,3-butanetricarboxylic acid, Disodium (3RS,4RS)-3-carboxy-4-hydroxy-4-[N-[(1RS,2RS)-1-methyl-2-(4-nitrophenyl)-3-{5-(phenylcarbamoyl)-2-furyl}propyl]-N-(2-naphthylmethyl)carbamoyl]butanoate, Disodium (3SR,4SR)-3-carboxy-4-hydroxy-4-[N-[(1RS,2RS)-1-methyl-2-(4-nitrophenyl)-3-{5-(phenylcarbamoyl)-2-furyl}propyl]-N-(2-naphthylmethyl)carbamoyl]butanoate, 3-tert-butoxycarbonyl-4-hydroxy-4-[N-[(1RS,2RS)-1-methyl-2-(4-nitrophenyl)-3-{5-(phenylcarbamoyl)-2-furyl}propyl]-N-(2-naphthylmethyl)carbamoyl]-3-butenoic acid, 3-tert-butoxycarbonyl-4-hydroxy-4-[N-[(1RS,2RS)-1-methyl-2-(3,4-methylenedioxyphenyl)-3-{5-(phenylcarbamoyl)-2-furyl}propyl]-N-(2-naphthylmethyl)carbamoyl]-3-butenoic acid, 3-tert-butoxycarbonyl-4-hydroxy-4-[N-{(1RS,2RS)-1-methyl-2-(4-nitrophenyl)-3-(3-phenoxymethylphenyl)propyl}-N-(2-naphthylmethyl)carbamoyl]-3-butenoic acid, 4-hydroxy-3-methoxycarbonyl-4-[N-(1RS,2RS)-1-methyl-2-(3,4-methylenedioxyphenyl)-3-{5-(phenylcarbamoyl)-2-furyl}propyl]-N-(2-naphthylmethyl)carbamoyl]-3-butenoic acid, 3-allyloxycarbonyl-4-hydroxy-4-[N-[(1RS,2RS)-1-methyl-2-(3,4-methylenedioxyphenyl)-3-{5-(phenylcarbamoyl)-2-furyl}propyl]-N-(2-naphthylmethyl)carbamoyl]-3-butenoic acid, 5-hydroxy-4-isopropoxycarbonyl-5-[N-[(1RS,2RS)-1-methyl-2-(4-nitrophenyl)-3-{5-(phenylcarbamoyl)-2-furyl}propyl]-N-(2-naphthylmethyl)carbamoyl]-4-pentenoic acid, and 3-tert-butoxycarbonyl-4-[N-(2,3-dichlorobenzyl)-N-[(1RS,2RS)-1-methyl-2-(4-nitrophenyl)-3-{5-(phenylcarbamoyl)-2-furyl}propyl]carbamoyl]-4-hydroxy-3-butenoic acid.

The compounds represented by general formula [I-a] or [I-b] are disclosed in Japanese Patent Applications JP6-210646, JP6-212147 and JP7-109067 and International Patent Publications WO96/05168 and WO96/05169 and have an inhibitory reactivity against protein-farnesyltransferase (PFT).

The compounds are a PFT inhibitor which compete with farnesyl pyrophosphate. According to the present invention, as the PFT inhibitor which competes with farnesyl pyrophosphate, in addition to these compounds, the PFT inhibitors disclosed in Drug Development Research, vol. 34, 121–137 (1995) may be mentioned.

The compounds represented by [I-a] or [I-b] used in the present invention are obtained through various reactions used for organic synthesis. Specifically, the methods disclosed in Japanese Patent Applications JP6-210646, JP6-212147 and JP7-109067 and International Patent Publications WO96/05168 and WO96/05169 can be used for their preparation.

The antitumor or anti-AIDS composition of the present invention suppresses the function of the Ras oncoprotein, and is useful as an antitumor agent or anti-AIDS agent, preferably as an antitumor agent for colon cancer, pancreatic cancer, myloid leukemia, lung cancer, carcinoma cutaneum, thyroid gland cancer and so on, articularly for pancreatic cancer.

The antitumor or anti-AIDS composition of the present invention is administered orally or parenterally as an antitumor agent or an anti-AIDS agent in the form of a pharmaceutical formulation suitable for the way of administration. The antitumor or anti-AIDS composition of the present invention may be clinically administered in the form of various pharmaceutical formulations containing pharmaceutically acceptable additives suitable for the way of administration. As the additives, various pharmaceutically common additives such as gelatin, lactose, saccharose, titanium oxide, starch, crystalline cellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropylcyclodextrin may be used.

The composition of the present invention may be formulations containing these additives, for example, solid formulations such as tablets, capsules, granules, powders or suppositories; or liquid formulations such as syrups, elixirs or injections. These formulations can be prepared in accordance with conventional methods commonly employed in the field of drug formulations. The liquid formulations may be solutions or suspensions in water or other appropriate solvents prepared just before administration. Especially, the injections may be solutions or suspensions in physiological saline or glucose solution depending on the case, and may contain a buffer or a preservative.

Such a pharmaceutical formulations contains a protein-farnesyltransferase inhibitor and an agent which decreases farnesyl pyrophosphate in vivo in a total amount of from 1.0 to 100 wt %, preferably from 1.0 to 60 wt %, based on the weight of the formulation, as active ingredients.

Such a formulation may contain other therapeutically effective compounds.

The weight ratio of the protein-farnesyltransferase inhibitor to the agent which decreases farnesyl pyrophosphate in vivo is within a range of from 0.001:1 to 1000:1, preferably from 0.01:1 to 100:1.

When the antitumor or anti-AIDS composition of the present invention is used as a medicine, the dose and the frequency of administration vary depending on the sex, age, weight, condition of the patient and the kind and extent of the desired therapeutic effect. However, in general, it is preferred to administer the composition to an adult at a daily dose of from 0.05 to 100 mg/kg once or several times a day in the case of oral administration, and at a daily dose of from 0.005 to 10 mg/kg once or several times a day in the case of parenteral administration.

BEST MODE FOR CARRYING OUT THE INVENTION

The present invention is now illustrated in greater detail by way of Examples, but it should be understood that the present invention is deemed to be limited thereto.

EXAMPLE 1

Formulation Example 1

To 2 parts of the compound prepared in Preparation Example 5 and 1 part of simvastatin, 97 parts of lactose was added and mixed well to prepare 100 parts of a powder. The powder was kneaded with a kneading liquid prepared by mixing 1 part of hydroxypropylcellulose and purified water and granulated. The granules were passed through a 20/mesh sieve, dried and sieved to a predetermined size.

EXAMPLE 2

Formulation Example 2

To 1 part of the compound prepared in Preparation Example 5 and 1 part of simvastatin, 20 parts of lactose and 5 parts of corn starch were added and mixed well. The resulting powder was granulated with ethanol by an ordinary method, dried and sieved, and 0.5% of magnesium stearate was admixed with it. The admixture was made into tablets containing the compound prepared in Preparation Example 5 and simvastatin in a total amount of 10 mg per tablet by an ordinary method.

EXAMPLE 3

Pharmacological Test Example 1

Inhibitory effect on farnesylation of Ras protein in NIH3T3 cells into which an activated ras gene was introduced, was measured by using the compounds prepared in Preparation Examples 3 and 5 as PFT inhibitors and L-654,969 (an active metabolite of simvastatin) as a hydroxymethylglutaryl CoA reductase inhibitor.

NIH3T3 cells into which an activated ras gene had been introduced were cultured on culture plates for 3 days, and each of the compounds prepared in Preparation Examples 3 and 5 was added at various concentrations alone or in combination with 0.15 $\mu$M or 5 $\mu$M of L-654,969 (at which concentration L-654,969 does not inhibit farnesylation of the Ras proteins by itself). The cells were cultured for 24 hours, peeled off the plates and dissolved in accordance with the method disclosed in J. Biol. Chem., vol. 268, 18415 (1993). The cell solutions were centrifuged at 12000 g for 5 minutes, and the supernatants were used as cell extracts. The cell extracts were subjected to SDS polyacrylamide gel electrophoresis to separate the farnesylated Ras protein and the unfarnesylated Ras protein. The proteins on the gel were transferred to nitrocellulose membranes and allowed to react with an anti-Ras protein antibody as the prove (the reaction of the primary antibody). After the anti-primary antibody, a peroxidaze-conjugated antibody (a secondary antibody) was allowed to react, the Ras protein was detected by mean of a chemoluminescence amplification kit. The proportion of the unfarnesylated Ras protein was determined by using a densitometer and defined as the inhibitory activity. As shown in Table 1 and Table 2, the inhibitory activities of the PFT inhibitors (the compounds of Preparation Example 3 or 5) on farnesylation of Ras proteins increased synergically and concentration-dependently in the presence of L-654,969.

TABLE 1

Inhibitory activity of the compound of Preparation Example 3 on farnesylation of the Ras proteins

| L-654,969 ($\mu$M) | Compound of Preparation Example 3 ($\mu$M) | Inhibitory rate (%) |
|---|---|---|
| None | 10 | 32 |
| | 3 | ND |
| | 1 | ND |
| 0.15 | 10 | 67 |
| | 3 | 27 |
| | 1 | ND |
| 5 | 10 | 90 |
| | 3 | 88 |
| | 1 | 55 |

TABLE 2

Inhibitory activity of the compound of Preparation Example 5 on farnesylation of the Ras proteins

| L-654,969 ($\mu$M) | Compound of Preparation Example 5 ($\mu$M) | Inhibitory rate (%) |
|---|---|---|
| None | 3 | 32 |
| | 1 | ND |
| | 0.3 | ND |
| 0.15 | 3 | 72 |
| | 1 | 18 |
| | 0.3 | ND |
| 5 | 3 | 95 |
| | 1 | 86 |
| | 0.3 | 43 |

ND: not detected

EXAMPLE 4

Pharmacological Test Example 2

Inhibitory activity on proliferation of BMJ1 cells was investigated by using the compounds prepared in Preparation Example 3, 4 or 5 and L-654,969. The BMJ1 cells which were obtained by introducing a hormone-inducible activated ras gene into BALB3T3 cells, a mouse-derived established cell line, were transformed by adding dexamethasone to the culture so as to produce an activated Ras protein. To assess the inhibitory effects of the PFT inhibitors on cell proliferation, the 50% proliferation inhibitory concentration for each compound was calculated by adding each compound to a transformed BMJ1 cell culture at various concentrations, and counting the number of cells after incubation. The cell numbers were counted in accordance with the SRB method disclosed in Proc. Am. Assoc. Cancer Res., vol. 30, 612 (1989). As shown in Table 3, the 50% cell proliferation inhibitory activities of the PFT inhibitors (the compounds of Preparation Examples 3 to 5) increased synergecally and concentration-dependently by the presence of 0.8 $\mu$M (at which concentration, L-654,969 does not inhibit cell proliferation alone) of L-654,969.

TABLE 3

Proliferation inhibitory action of combined use of PFT inhibitors and L-654,969

| | 50% Proliferation inhibitory concentration (IC$_{50}$ $\mu$M) | |
|---|---|---|
| Compound | In the absence of L-654,969 | In the presence of 0.8 $\mu$M of L-654,969 |
| Compound of Preparation Example 3 | 130 | 11 |
| Compound of Preparation Example 4 | 105 | 6.5 |
| Compound of Preparation Example 5 | 3.1 | 0.93 |

PREPARATION EXAMPLE 1

Preparation of (2R*)-2-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]succinic acid and (2R*)-2-[N-{(1RS,2RS,4Z)-5-(2-benzoxazolyl)-1-methyl-2-(3,4-methylenedioxyphenyl)-4-pentenyl}-N-(2-naphthylmethyl)carbamoylmethyl]succinic acid (1) Preparation of di-tert-butyl (2R*)-2-[N-{(1RS,2RS)-4,4-diethoxy-1-methyl-2-(3,4-methylenedioxyphenyl)butyl}-N-(2-naphthylmethyl)carbamoylmethyl]succinate 436 mg of N-{(1RS,2RS)-4,4-diethoxy-1-methyl-2-(3,4-methylenedioxyphenyl)butyl}-2-naphthymethylamine, 346 mg of 1,2-di-tert-butyl (R*)-1,2,3-propanetricarboxylate prepared in Reference Example 1 and 122 mg of 4-dimethylaminopyridine were dissolved in 5 ml of methylene chloride, and stirred with 249 mg of 1-ethyl-3-(3-dimethylaminopropyl)carbodiimide hydrochloride at room temperature for 14 hours. The reaction solution was diluted with ethyl acetate, then washed successively with 1N hydrochloric acid, saturated aqueous sodium hydrogencarbonate and saturated aqueous sodium chloride and dried over anhydrous magnesium sulfate. The desiccant was filtered off, and the solvent was evaporated in vacuo. The residue was purified by silica gel column chromatography [hexane/ethyl acetate=10/1→5/1] to give 636 mg (yield 90%) of the title compound as a colorless foamy substance.

(2) Preparation of di-tert-butyl (2R*)-2-[N-{(1RS,2RS)-3-formyl-1-methyl-2-(3,4-methylenedioxyphenyl)propyl}-N-(2-naphthylmethyl)carbamoylmethyl]succinate 636 mg of di-tert-butyl (2R*)-2-[N-{(1RS,2RS)-4,4-diethoxy-1-methyl-2-(3,4-methylenedioxyphenyl)butyl}-N-(2-naphthylmethyl)carbamoylmethyl]succinate was dissolved in 12 ml of tetrahydrofuran and stirred with 3 ml of 2N hydrochloric acid at room temperature for 3 hours. After addition of saturated aqueous sodium hydrogencarbonate, the reaction solution was extracted with ethyl acetate. The organic layer was washed with saturated aqueous sodium chloride and dried over anhydrous magnesium sulfate. The desiccant was filtered off, and the solvent was evaporated in vacuo to give 567 mg (stoichiometrical yield) of the title compound as a colorless oily substance.

(3) Preparation of di-tert-butyl (2R*)-2-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]succinate 53 mg of 60% oily sodium hydride suspended in 5 ml of tetrahydrofuran was stirred with 634 mg of 2-benzoxazolylmethyl(triphenyl)phosphonium bromide at room temperature for 30 minutes. 563 mg of di-tert-butyl (2R*)-2-[N-{(1RS,2RS)-3-formyl-1-methyl-2-(3,4-methylenedioxyphenyl)propyl}-N-(2-naphthylmethyl)carbamoylmethyl]succinate in 5 ml of tetrahydrofuran was added, and the reaction solution was stirred at room temperature for 12 hours. After addition of water, the reaction solution was extracted with ethyl acetate. The organic layer was washed with saturated aqueous sodium chloride and dried over anhydrous magnesium sulfate. The desiccant was filtered off, and the solvent was evaporated in vacuo. The residue was purified by silica gel column chromatography [hexane/ethyl acetate=10/1→5/1] to give 528 mg (yield 79%) of the title compound and 105 mg (yield 16%) of the Z-isomer of the title compound as colorless foamy solids.

(4) Preparation of (2R*)-2-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]succinic acid 486 mg of di-tert-butyl (2R*)-2-[N-{(1RS,2RS,4E)-5-(2-benzoxazolyl)-1-methyl-2-(3,4-methylenedioxyphenyl)-4-pentenyl}-N-(2-naphthylmethyl)carbamoylmethyl]succinate in 10 ml of formic acid was stirred at room temperature for 12 hours. The formic acid was evaporated in vacuo, leaving 412 mg (stoichiometrical yield) of the title compound as a white solid.

$^1$H-NMR(CDCl$_3$)δ: 0.91–1.00 (3H,m), 2.30–3.70(8H,m), 4.20–5.30(3H,m), 5.90–5.94(2H,m), 6.43(1H,d,J=15.7 Hz), 6.57–6.76(4H,m), 7.26–7.84(11H,m); FAB-MS: 635(M+H).

The above-mentioned procedure was performed with di-tert-butyl (2R*)-2-[N-{(1RS,2RS,4Z)-5-(2-benzoxazolyl)-1-methyl-2-(3,4-methylenedioxyphenyl)-4-pentenyl}-N-(2-naphthylmethyl)carbamoylmethyl] succinate to give the Z-isomer of the title compound.

PREPARATION EXAMPLE 2

Preparation of 4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-1,2,3-butanetricarboxylic acid (1) Preparation of triethyl 4-[N-{(1RS,2RS,4E)-4,4-diethoxy-1-methyl-2-(3,4-methylenedioxyphenyl)-4-pentenyl}-N-(2-naphthylmethyl)carbamoyl]-1,2,3-butanetricarboxylate 80 mg of N-{(1RS,2RS)-4,4-diethoxy-1-methyl-2-(3,4-methylenedioxyphenyl)butyl}-2-naphthylmethylamine, 100 mg of 2,3,4-triethyl 1,2,3,4-butanetetracarboxylate prepared in Reference Example 2 and 27 mg of 4-dimethylaminopyridine were dissolved in 5 ml of methylene chloride and stirred with 43 mg of 1-ethyl-3-(3-dimethylaminopropyl)carbodiimide hydrochloride at room temperature overnight. The reaction solution was diluted with ethyl acetate, then washed successively with 1N hydrochloric acid, saturated aqueous sodium hydrogencarbonate and saturated aqueous sodium chloride and dried over anhydrous magnesium sulfate. The desiccant was filtered off, and the solvent was evaporated in vacuo. The residue was roughly purified by silica gel column chromatography [ethyl acetate] and purified by medium pressure liquid chromatography [Lobar column™, size B, Lichroprep™Si60 (Merck & Co., Inc.); hexane/ethyl acetate=2/1] to give 54 mg (yield 40%) of the title compound as a colorless foamy solid.

(2) Preparation of 4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-1,2,3-butanetricarboxylic acid The N-acylated product obtained in (1) was converted to triethyl 4-[N-{(1RS,2RS,4E)-5-(2-benzoxazolyl)-1-methyl-2-(3,4-methylendioxyphenyl)-4-pentenyl}-N-(2-naphthylmethyl)carbamoyl]-1,2,3-butanetricarboxylate in the same manner as in Preparation Example 1. The resulting ester was dissolved in 1 ml of tetrahydrofuran, and after addition of 0.5 ml of 3N sodium hydroxide, it was left standing at room temperature overnight. The reaction solution was diluted with ethyl acetate, acidified with 1N hydrochloric acid, washed with saturated aqueous sodium chloride and dried over anhydrous magnesium sulfate. The desiccant was filtered off, and the solvent was evaporated in vacuo. The residue was purified by medium pressure liquid chromatography [Lobar column™, size A, RP-8 (Merck & Co., Inc.); acetonitrile/0.1% aqueous trifluoroacetic acid=1/1] to give 14 mg (yield 52%) of the title compound as a white powder.

$^1$H-NMR(CDCl$_3$+CD$_3$OD)δ: 0.80–1.00(3H,m), 2.30–3.75(9H,m), 4.20–5.30(3H,m), 5.85–5.95(2H,m), 6.40–6.80(5H,m), 7.20–7.50(6H,m), 7.55–7.85(5H,m); FAB-MS: 693(M+H).

The compound of Preparation Example 3 was prepared in the same manner as in Preparation Example 2 by using the corresponding carboxylic acid derivative instead of the 2,3,4-triethyl 1,2,3,4-butanetetracarboxylate as the starting material.

PREPARATION EXAMPLE 3

3-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-1,2,2-propanetricarboxylic acid $^1$H-NMR(CD$_3$COCD$_3$)δ: 0.82–1.04(3H,m), 2.50–3.90 (7H,m), 5.93–7.97(21H,m); FAB-MS: 679(M+H).

PREPARATION EXAMPLE 4

Preparation of disodium (3RS,4RS)-4-[N-{(1RS, 2RS,4E)-5-(2-benzoxazolyl)-1-methyl-2-(3,4-methylenedioxyphenyl)-4-pentenyl}-N-(2-naphthylmethyl)carbamoyl]-3-carboxylato-4-hydroxybutanoate (1) Preparation of (2RS,3RS)-2-[N-{(1RS,2RS,4E)-5-(1-benzoxazolyl)-1-methyl-2-(3,4-methylenedioxyphenyl)-4-pentenyl}-N-(2-naphthylmethyl)carbamoyl]-5-oxotetrahydrofuran-3-carboxylic acid 47 mg of tert-butyl (2RS,3RS)-2-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-5-oxotetrahydrofuran-3-carboxylate [synthesized from N-{(1RS,2RS)-4,4-diethoxy-1-methyl-2-(3,4-methylenedioxyphenyl)butyl}-2-naphthylmethylamine and (2RS,3RS)-3-tert-butoxycarbonyl-5-oxotetrahydrofuran-2-carboxylic acid in the same manner as in Preparation Example 1] was dissolved in 1 ml of formic acid, and was left standing at room temperature overnight. The reaction solution was evaporated in vacuo, and toluene was added to the residue and evaporated. The resulting residue was purified by silica gel column chromatography [hexane/ethyl acetate=2/1→chloroform/methanol=50/1] to give 20 mg (yield 46%) of the title compound as a white solid.

$^1$H-NMR(CDCl$_3$)δ: 0.99 and 1.10 (total 3H, each d,J=6.2 Hz, 6.3 Hz), 2.50–3.10(5H,m), 4.15–4.25 and 4.37–4.47 (total 1H, each m), 4.50–5.35 (4H,m), 5.73, 5.75, 5.88 and 5.94 (total 2H, each s), 6.07 and 6.36 (total 1H, each d,J=15.8 Hz, 15.8 Hz), 6.60–6.75(4H,m), 7.25–7.82 (11H, m); FAB-MS: 633(M+H).

(2) Disodium (3RS,4RS)-4-[N-{(1RS,2RS,4E)-5-(2-benzoxazolyl)-1-methyl-2-(3,4-methylenedioxyphenyl)-4-pentenyl}-N-(2-naphthylmethyl)carbamoyl]-3-carboxylato-4-hydroxybutanoate 8 mg of the lactone obtained above was dissolved in a mixture of 1 ml of methanol and 1 ml of tetrahydrofuran, and 26 μl of 1N aqueous sodium hydroxide was added under cooling with ice with stirring. The reaction solution was stirred at room temperature for 10 minutes and evaporated in vacuo to dryness to give 10 mg (stoichiometrical yield) of the title compound as a white solid.

$^1$H-NMR(CDCl$_3$)δ: 0.91 and 1.03(total 3H, each d,J=6.0 Hz, 6.7 Hz), 2.35–3.40(6H,m), 4.60–5.10(4H,m), 5.86 and 5.90(total 2H, each s), 6.00 and 6.93(5H, each m), 7.28–8.01 (11H,m); FAB-MS: 695(M+H).

PREPARATION EXAMPLE 5

Preparation of 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxy-3-butenoic acid (1) Preparation of methyl (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxybutanoate 193 mg of tert-butyl (2S,3S)-2-[N-{(1R,2R,4E)-5-(2-benzoxazoyl)-1-methyl-2-(3,4-methylenedioxyphenyl)-4-pentenyl}-N-(2-naphthylmethyl)carbamoyl]-5-oxotetrahydrofuran-3-carboxylate [synthesized from N-{(1R,2R)-4,4-diethoxy-1-methyl-2-(3,4-methylenedioxyphenyl)butyl}-2-naphthylamine prepared in Reference Example 5 and (2S,3S)-3-tert-butoxycarbonyl-5-oxotetrahydrofuran-2-carboxylic acid obtained in Reference Example 4, in the same manner as in Preparation Example 1] in a mixture of 5 ml of tetrahydrofuran and 2 ml of water was stirred with 0.31 ml of 1N aqueous sodium hydroxide at room temperature for 15 hours. The reaction solution was acidified (to about pH 4) with 1N hydrochloric acid and extracted with ethyl acetate. The extract was dried over anhydrous magnesium sulfate, the desiccant was filtered off, and the solvent was evaporated in vacuo. The resulting carboxylic acid was dissolved in ethyl acetate, and a small excess of diazomethane was added at room temperature. The solvent was evaporated in vacuo, and the residue was purified by silica gel column chromatography [hexane/ethyl acetate=2/1] to give 202 mg (stoichiometrical yield) of the title compound as a colorless oily substance.

(2) Preparation of methyl 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxy-3-butenoate 36 mg of methyl (3S,4S)-4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxybutanoate in 2 ml of chloroform was stirred with 42 mg of the Dess-Martin reagent (periodenane) at room temperature for 1 hour. The reaction solution was poured into a mixture of saturated aqueous sodium hydrogencarbonate and saturated aqueous sodium thiosulfate and extracted with ethyl acetate. The organic layer was washed with saturated aqueous sodium chloride and dried over anhydrous magnesium sulfate. The desiccant was filtered off, and the solvent was evaporated in vacuo. The residue was purified by silica gel thin layer chromatography [Kieselgel™ 60F$_{254}$, Art™ 5744; hexane/ethyl acetate=3/2] to give 14.7 mg (yield 41%) of the title compound as a colorless oily substance.

(3) Preparation of 4-[N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxy-3-butenoic acid 9.9 mg of methyl 4-N-{(1R,2R,4E)-5-(2-benzoxazolyl)-1-methyl-2-(3,4-methylenedioxyphenyl)-4-pentenyl}-N-(2-naphthylmethyl)carbamoyl]-3-tert-butoxycarbonyl-4-hydroxy-3-butenoate in a mixture of 3 ml of tetrahydrofuran and 1 ml of water was stirred with 140 μl of 1N aqueous sodium hydroxide at room temperature for 4 hours. The reaction solution was acidified with 1N hydrochloric acid and extracted with ethyl acetate. The extract was dried over anhydrous magnesium sulfate, the desiccant was filtered off, and the solvent was evaporated in vacuo. The residue was purified by silica gel thin layer chromatography [Kieselgel™ 60F$_{254}$, Art™ 5744; chloroform/methanol=10/1] to give 6.9 mg (yield 70%) of the title compound as a colorless foamy substance.

$^1$H-NMR(CDCl$_3$)δ: 0.96–1.06(3H,m), 1.41–1.51(9H,m), 2.30–3.29(5H,m), 4.15–4.98(4H,m), 5.88–6.34(3H,m), 6.41–6.74(4H,m), 7.21–7.88(11H,m); FAB-MS: 705(M+H).

REFERENCE EXAMPLE 1

Preparation and optical resolution of 1,2-di-tert-butyl 1,2,3-propanetricarboxylate 13.1 ml of 1.5M cyclohexane solution of lithium diisopropylamide was dissolved in 10 ml of tetrahydrofuran, and a tetrahydrofuran solution (10 ml) of 2.96 g of benzyl acetate was added under cooling at −70° C. with stirring. The resulting solution was stirred at the same temperature for 30 minutes. Then, a tetrahydrofuran solution (10 ml) of 2.96 g of di-tert-butyl maleate was added dropwise, and the solution was stirred at the same temperature for 30 minutes. 20 ml of water and 50 ml of ethyl ether were added to the reaction solution for extraction. The organic layer was separated, washed with saturated aqueous sodium chloride and dried over anhydrous magnesium sulfate, and the solvent was evaporated in vacuo. The residue was dissolved in 50 ml of dioxane and catalytically reduced with 0.4 g of a 10% palladium-carbon catalyst at room temperature at atmospheric pressure of hydrogen for 20 hours. The catalyst was filtered off, and the solvent was evaporated in vacuo. The residue was precipitated in hexane and the precipitate was collected by filtration and dried to give 3.02 g of the title compound as a colorless crystalline powder, mp 55–57° C.

12.97 g of the di-tert-butyl ester thus obtained and 13.24 g of cinchonidine were dissolved in 1L of carbon tetrachloride by heating, and the solution was seeded and left standing at room temperature for 24 hours. The crystals were collected by filtration, and dissolution of the crystals in 1L of hot carbon tetrachloride and seeding of the solution followed by 24 hours of standing at room temperature were repeated two more times to obtain 6.66 g of the cinchonidine salt of the title compound, which was designated as the (S*)-isomer for the sake of convenience, $[\alpha]_D^{20}$ −62.7° (c 1.0 chloroform).

The cinchonidine salt thus obtained was dissolved in a mixture of ethyl ether and 1N hydrochloric acid cooled with ice, and the organic layer was separated and post-treated by a usual method to give the (S*)-isomer of the title compound as a colorless oily substance, $[\alpha]_D^{20}$ +4.44° (c 0.92 chloroform).

The cinchonidine salt of the other enantiomer which was contained abundantly in the other fraction obtained during the above optical resolution was converted to the free acid and treated with quinine in isopropylether in a similar manner to give the enantiomer, which was designated as the (R*)-isomer for the sake of convenience.

REFERENCE EXAMPLE 2

Preparation of 2,3,4-triethyl (2RS,3SR)-1,2,3,4-butanetetracarboxylate 1.17 g of tetraethyl (2RS,3SR)- 1,2,3,4-butanetetracarboxylate was dissolved in a mixture of 5 ml of ethanol and 5 ml of water, and stirred with 142 mg of lithium hydroxide monohydrate at room temperature overnight. The ethanol was evaporated in vacuo, and diethyl ether was added to the residual solution for partitioning. The aqueous layer was separated, acidified with 1N hydrochloric acid and extracted with diethyl ether. The organic layer was dried over anhydrous magnesium sulfate, the desiccant was filtered off, and the solvent was evaporated in vacuo. The residue was purified by silica gel column chromatography [chloroform/methanol=100/1→30/1] to give 460 mg of the title compound as a colorless oily substance.

REFERENCE EXAMPLE 3

Preparation of (2RS,3RS)-3-tert-butoxycarbonyl-5-oxotetrahydrofuran-2-carboxylic acid
(1) Preparation of (2RS,3SR)-2-diphenylmethoxycarbonyl-5-oxotetrahydrofuran-3-carboxylic acid 262 mg of (2RS,3SR)-5-oxotetrahydrofuran-2,3-dicarboxylic acid in 5 ml of acetone was stirred with 291 mg of diphenyldiazomethane at room temperature for 20 minutes. The reaction solution was evaporated in vacuo to dryness. The residue was purified by silica gel column chromatography [chloroform/methanol=100/1→10/1] to give 163 mg of the title compound as a white powder.

(2) Preparation of 3-tert-butyl 2-diphenylmethyl (2RS,3RS)-5-oxotetrahydrofuran-2,3-dicarboxylate 163 mg of (2RS,3SR)-2-diphenylmethoxycarbonyl-5-oxotetrahydrofuran-3-carboxylic acid, 59 mg of 4-dimethylaminopyridine and 36 mg of tert-butanol in 4 ml of methylene chloride were stirred with 110 mg of 1-ethyl-3-(3-dimethylaminopropyl)carbodiimide hydrochloride at room temperature for 13 hours. The reaction solution was diluted with methylene chloride, washed successively with 10% aqueous citric acid, saturated aqueous sodium hydrogencarbonate and saturated aqueous sodium chloride and dried over anhydrous magnesium sulfate. The desiccant was filtered off, the solvent was evaporated in vacuo. The residue was purified by silica gel column chromatography [hexane/ethyl acetate=10/1] to give 148 mg of the title compound as a colorless oily substance.

(3) Preparation of (2RS,3RS)-3-tert-butoxycarbonyl-5-oxotetrahydrofuran-2-carboxylic acid 148 mg of 3-tert-butyl 2-diphenylmethyl (2RS,3RS)-5-oxotetrahydrofuran-2,3-dicarboxylate in 4 ml of ethyl acetate was catalytically reduced with 15 mg of a 10% palladium-carbon catalyst at room temperature at atmospheric pressure of hydrogen for 15 hours. The catalyst was filtered off, and the solvent was evaporated in vacuo. The residue was washed with benzene to give 66 mg of the title compound as a white crystalline powder.

REFERENCE EXAMPLE 4

Preparation of (2S,3S)-3-tert-butoxycarbonyl- 5-oxotetrahydrofuran-2-carboxylic acid
(1) Preparation of 3-tert-butyl 1,2-diethyl (1S,2R)-1-hydroxy-1,2,3-propanetricarboxylate 31 ml of 1.69M hexane solution of n-butyllithium was dissolved in 30 ml of tetrahydrofuran, and 7.1 ml of diisopropylamine was added under cooling with ice. The resulting solution was stirred at the same temperature for 30 minutes and then cooled to −78° C. 4.94 g of diethyl (S)-malate in 20 ml of tetrahydrofuran was added dropwise at or below −50° C., and the resulting reaction solution was stirred at −20° C. for 1.5 hours. The reaction solution was cooled to −78° C., and a solution of 5.58 g of tert-butyl bromoacetate and 4.66 g of hexamethylphosphoric triamide in 20 ml of tetrahydrofuran was added dropwise at or below −50° C. The resulting reaction solution was stirred at room temperature for 1 hour. The reaction solution was poured into 150 ml of 0.5N hydrochloric acid and extracted with diethyl ether, and the organic layer was washed with saturated aqueous sodium hydrogencarbonate and saturated aqueous sodium chloride and dried over anhydrous magnesium sulfate. The desiccant was filtered off, the solvent was evaporated in vacuo. The residue was purified by silica gel column chromatography [hexane/ethyl acetate=5/1→4/1] to give 3.88 g of the title compound as a yellow oily substance.
(2) Preparation of (2S,3R)-5-oxotetrahydrofuran-2,3-dicarboxylic acid 16.49 g of 3-tert-butyl 1,2-diethyl (1S,2R)-1-hydroxy-1,2,3-propanetricarboxylate, 100 ml of acetic acid and 50 ml of concentrated hydrochloric acid were mixed and stirred at 70° C. for 5 hours. The acetic acid and hydrochloric acid were evaporated in vacuo, and the residue was dissolved in 100 ml of acetic acid and 50 ml of concentrated hydrochloric acid again. The resulting solution was stirred at 70° C. for 12 hours. The acetic acid and hydrochloric acid were evaporated in vacuo, and the residue was stirred in 100 ml of trifluoroacetic acid at 60° C. for 5 hours. The trifluoroacetic acid was evaporated in vacuo, and the residue was crystallized in hexane-ethyl acetate to give 9.38 g of the title compound as a white powder.

(3) Preparation of (2S,3R)-2-benzyloxycarbonyl-5-oxotetrahydrofuran-3-carboxylic acid 5.2 g of (2S,3R)-5-oxotetrahydrofuran-2,3-dicarboxylic acid in 88 ml of acetone was stirred with 6.5 g of 1,1'-dicyclohexylcarbodiimide at room temperature for 2 hours. 3.26 ml of benzyl alcohol was added, and the reaction solution was stirred at the same temperature for 12 hours. The insolubles were filtered off, the filtrate was concentrated in vacuo. The residue was purified by silica gel column chromatography [hexane/ethyl acetate=4/1→chloroform/methanol=50/1] to give 7.93 g of the title compound as a yellow solid.

(4) Preparation of 2-benzyl 3-tert-butyl (2S,3S)-5-oxotetrahydrofuran-2,3-dicarboxylate To 7.93 g of (2S,3R)-2-benzyloxycarbonyl-5-oxotetrahydrofuran-3-carboxylic acid in 75 ml of chloroform, 5.5 g of 4-dimethylaminopyridine, 8.6 g of 1-ethyl-3-(3-dimethylaminopropyl)carbodiimide hydrochloride and 5.7 ml of tert-butyl alcohol were successively added, and the resulting reaction solution was stirred at room temperature for 60 hours. The reaction solution was poured into 1N hydrochloric acid cooled with ice and extracted with ethyl acetate. The organic layer was dried over anhydrous magnesium sulfate, the desiccant was filtered off, the solvent was evaporated in vacuo, and the residue was purified by silica gel column chromatography [hexane/ethyl acetate=5/1] to give 6.48 g of the title compound as a white solid.

(5) Preparation of (2S,3S)-3-tert-butoxycarbonyl-5-oxotetrahydrofuran-2-carboxylic acid 6.4 g of 2-benzyl 3-tert-butyl (2S,3S)-5-oxotetrahydrofuran-2,3-dicarboxylate in 80 ml of ethyl acetate was catalytically reduced with 640 mg of a 10% palladium-carbon catalyst at room temperature at atmospheric pressure of hydrogen for 3 hours. The catalyst was filtered off, and the filtrate was evaporated to dryness to give 4.39 g of the title compound as a white solid.

REFERENCE EXAMPLE 5

Preparation of N-{(1R,2R)-4,4-diethoxy-1-methyl-2-(3,4-methylenedioxyphenyl)butyl}-2-naphthylmethylamine (1) Preparation of 5,5-diethoxy-3-(3,4-methylenedioxyphenyl)pentan-2-one To 11.7 g of 3,4-methylenedioxyphenylacetone in 100 ml of dimethylformamide, 2.76 g of 60% oily sodium hydride was added under cooling with ice with stirring, and after stirring at the same temperature for 30 minutes, 20.9 g of iodoacetaldehyde diethyl acetal in 20 ml of dimethylformamide was added. The reaction solution was stirred at room temperature for 2 hours and partitioned between water and ethyl ether. The organic layer was washed with saturated aqueous sodium chloride and then dried over anhydrous magnesium sulfate. The desiccant was filtered off, and the solvent was evaporated in vacuo. The residue was purified by silica gel column chromatography [hexane/ethyl acetate=15/1→10/1] to give 18.3 g of the title compound.

(2) Preparation of (2RS,3SR)-5,5-diethoxy-3-(3,4-methylenedioxyphenyl)pentan-2-ol To 18.3 g of 5,5-diethoxy-3-(3,4-methylenedioxyphenyl)pentan-2-one in 200 ml of tetrahydrofuran, 65 ml of 1M tetrahydrofuran solution of lithium tri-sec-butylborohydride was added under cooling at −78° C. with stirring, and the resulting solution was stirred at the same temperature for 1 hour. To the reaction solution stirred and cooled with ice, 109 ml of 3N aqueous sodium hydroxide was added, and then 48 ml of 30% aqueous hydrogen peroxide was gradually added dropwise. The reaction solution was stirred at room temperature for 1 hour and partitioned between ethyl ether and water. The organic layer was washed with saturated aqueous sodium thiosulfate and saturated aqueous sodium chloride and dried over anhydrous magnesium sulfate. The desiccant was filtered off, and the solvent was evaporated in vacuo. The residue was purified by silica gel column chromatography [hexane/ethyl acetate=10/1→3/1] to give 16.8 g of the title compound.

(3) Preparation of (2S,3R)-5,5-diethoxy-3-(3,4-methylenedioxyphenyl)pentan-2-ol

To 31.98 g of (2RS,3SR)-5,5-diethoxy-3-(3,4-methylenedioxyphenyl)pentan-2-ol in 320 ml of vinyl acetate, 15.1 ml of triethylamine was added. The resulting reaction solution was stirred with 1.0 g of immobilized lipase (Toyozyme LIP) at 30° C. for 16 hours. After 0.9 g of immobilized lipase was further added, the solution was stirred at the same temperature for 46 hours. The insolubles were filtered off, and the filtrate was diluted with ethyl acetate, washed successively with 1N hydrochloric acid, saturated aqueous sodium hydrogencarbonate and saturated aqueous sodium chloride and dried over anhydrous magnesium sulfate. The desiccant was filtered off, and the solvent was evaporated in vacuo. The residue was purified by silica gel column chromatography [hexane/ethyl acetate=5/1→1/1] to give 18.40 g of (2R,3S)-2-acetoxy-5,5-diethoxy-3-(3,4-methylenedioxyphenyl)pentane and 16.05 g of the title compound as colorless oily substances.

(4) Preparation of (1R,2R)-4,4-diethoxy-1-methyl-2-(3,4-methylenedioxy)phenylbutylamine To 15.2 g of (2S,3R)-5,5-diethoxy-3-(3,4-methylenedioxyphenyl)pentan-2-ol in 130 ml of ethyl acetate cooled with ice, 14.0 ml of triethylamine and 6.0 ml of methanesulfonyl chloride were added with stirring, and the resulting reaction solution was stirred at the same temperature for 30 minutes. After addition of saturated aqueous sodium hydrogencarbonate, the reaction solution was vigorously stirred at room temperature for 30 minutes and then extracted with ethyl acetate. The organic layer was washed with saturated aqueous sodium chloride and dried over anhydrous magnesium sulfate. The desiccant was filtered off, and the solvent was evaporated in vacuo. Then, the residue was dissolved in 100 ml of dimethylformamide and heated with 16.7 g of sodium azide at 120° C. for 1 hour with stirring. The reaction solution was allowed to cool to room temperature and partitioned between ethyl ether and water. The organic layer was separated and washed with saturated aqueous sodium chloride, and the solvent was evaporated in vacuo. The resulting residue was refluxed with 13.5 g of triphenylphosphine in 110 ml of tetrahydrofuran containing 10% of water under heating for 4 hours. The reaction solution was evaporated to dryness in vacuo, and the residue was purified by silica gel column chromatography [ethyl acetate→ethyl acetate/methanol=10/1] to give 11.8 g of the title compound.

(5) Preparation of N-{(1R,2R)-4,4-diethoxy-1-methyl-2-(3,4-methylenedioxyphenyl)butyl}-2-naphthylmethylamine 11.8 g of (1R,2R)-4,4-diethoxy-1-methyl-2-(3,4-methylenedioxy)phenylbutylamine in 80 ml of methanol, was stirred with 5.98 g of 2-naphthaldehyde at 600° C. for 3 hours. The reaction solution was cooled to 0° C. and stirred with 2.27 g of sodium borohydride at room temperature for 1 hour. The reaction solution was poured into water and extracted with ethyl acetate. The organic layer was washed with saturated aqueous sodium chloride and dried over anhydrous magnesium sulfate. The desiccant was filtered off, and the solvent was evaporated in vacuo. The residue was purified by silica gel column chromatography [hexane/ethyl acetate=10/1→2/1] to give 16.6 g of the title compound.

INDUSTRIAL APPLICABILITY

The antitumor or anti-AIDS composition of the present invention suppresses the function of the Ras oncoproteins remarkably by virtue of the combination of a protein-farnesyltransferase inhibitor and an agent which decreases farnesyl pyrophosphate in vivo, and is useful as antitumor or anti-AIDS agent.

We claim:

1. An antitumor or anti-AIDS composition containing a protein-farnesyltransferase inhibitor and an agent which decreases farnesyl pyrophosphate in vivo as active ingredients.

2. The antitumor or anti-AIDS composition according to claim 1, wherein the agent which decreases farnesyl pyrophosphate in vivo is a farnesyl pyrophosphate biosynthesis inhibitor.

3. The antitumor or anti-AIDS composition according to claim 2, wherein the farnesyl pyrophosphate biosynthesis inhibitor is a hydroxymethylglutaryl CoA reductase inhibitor.

4. The antitumor or anti-AIDS composition according to claim 3, wherein the hydroxymethylglutaryl CoA reductase inhibitor is lovastatin, simvastatin, pravastatin or fluvastatin.

5. The antitumor or anti-AIDS composition according to claim 1, wherein the protein-farnesyltransferase inhibitor is a competitive inhibitor which competes with farnesyl pyrophosphate.

6. The antitumor or anti-AIDS composition according to claim 1, wherein the protein-farnesyltransferase inhibitor is a compound represented by general formula or a pharmaceutically acceptable salt or ester thereof:

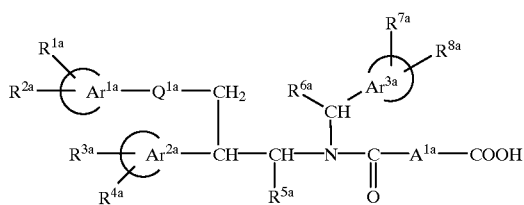

[I-a]

wherein each of

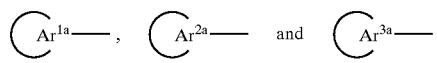

which may be the same or different is an aryl group or an aromatic heterocyclic group; $A^{1a}$ is a saturated or unsaturated aliphatic $C_{2-8}$ hydrocarbon group which may have substituents selected from the group consisting of lower alkyl groups, hydroxyl groups, lower hydroxyalkyl groups, lower alkoxy groups, carboxyl groups, lower carboxyalkyl groups, aryl groups and aralkyl groups; $Q^{1a}$ is —$(CH_2)_m$— (wherein m is an integer of from 1 to 6) or —$(CH_2)_n$—$W^{1a}$—$(CH_2)_p$— (wherein $W^{1a}$ is an oxygen atom, a sulfur atom, a vinylene group or an ethynylene group; each of n and p which may be the same or different is an integer of from 0 to 3); $R^{1a}$ is a hydrogen atom, a halogen atom, a hydroxyl group, a lower alkyl group, a lower alkoxy group or an aryl or aromatic heterocyclic group which may have substituents selected from the group consisting of halogen atoms, lower alkyl groups and lower alkoxy groups; each of $R^{2a}$, $R^{7a}$ and $R^{8a}$ which may be the same or different is a hydrogen atom, a halogen atom, a hydroxyl group, a lower alkyl group or a lower alkoxy group; each of $R^{3a}$ and $R^{4a}$ which may be the same or different is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^{5a}$ is a lower alkyl group; and $R^{6a}$ is a hydrogen atom or a lower alkyl group.

7. The antitumor or anti-AIDS composition according to claim 1, wherein the protein-farnesyltransferase inhibitor is a compound represented by general formula or a pharmaceutically acceptable salt or ester thereof:

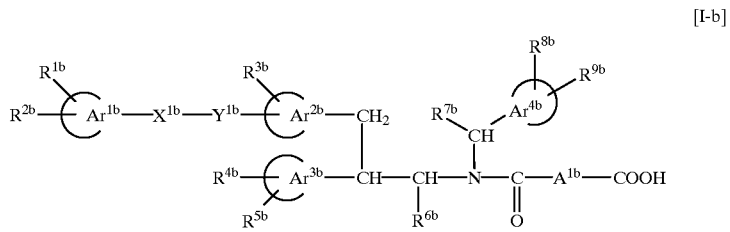

[I-b]

wherein each of

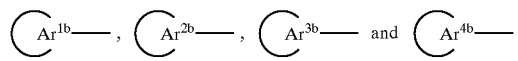

which may be the same or different is an aryl group or an aromatic heterocyclic group; $A^{1b}$ is a saturated or unsaturated aliphatic $C_{2-8}$ hydrocarbon group which may have substituents selected from the group consisting of lower alkyl groups, hydroxyl groups, lower hydroxyalkyl groups, lower alkoxy groups, carboxyl groups, lower carboxyalkyl groups, aryl groups and aralkyl groups; each of $X^{1b}$ and $Y^{1b}$ which may be the same or different is an oxygen atom, a sulfur atom, a carbonyl group, —$CHR^{10b}$— (wherein $R^{10b}$ is a hydrogen atom or a lower alkyl group) or —$NR^{11b}$— (wherein $R^{11b}$ is a hydrogen atom or a lower alkyl group), or $X^{1b}$ and $Y^{1b}$ together represent a vinylene group or an ethynylene group; each of $R^{1b}$, $R^{2b}$, $R^{3b}$, $R^{8b}$ and $R^{9b}$ which may be the same or different is a hydrogen atom, a halogen atom, a hydroxyl group, a lower alkyl group or a lower alkoxy group; each of $R^{4b}$ and $R^{5b}$ which may be the same or different is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^{6b}$ is a lower alkyl group; and $R^{7b}$ is a hydrogen atom or a lower alkyl group, provided that when either $X^{1b}$ or $Y^{1b}$ is an oxygen atom, a sulfur atom or —$NR^{11b}$— (wherein $R^{11b}$ is the same as defined above), the other is a carbonyl group or —$CHR^{10b}$— (wherein $R^{10b}$ is the same as defined above).

8. The antitumor or anti-AIDS composition according to claim 1, wherein the weight ratio of the protein-farnesyltransferase inhibitor and the agent which decreases farnesyl pyrophosphate in vivo is from 0.001:1 to 1000:1.

9. An antitumor or anti-AIDS composition containing a protein-farnesyltransferase inhibitor and an agent which decreases farnesyl pyrophosphate in vivo as active ingredients, wherein the protein-farnesyltransferase inhibitor is a compound represented by general formula or a pharmaceutically acceptable salt or ester thereof:

[I-a]

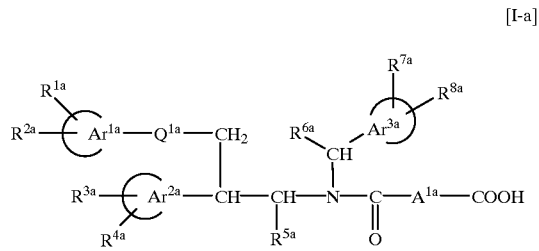

wherein each of

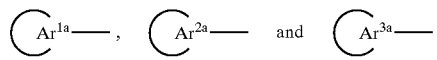

which may be the same or different is an aryl group or an aromatic heterocyclic group; $A^{1a}$ is a saturated or unsaturated aliphatic $C_{2-8}$ hydrocarbon group which may have substituents selected from the group consisting of lower alkyl groups, hydroxyl groups, lower hydroxyalkyl groups, lower alkoxy groups, carboxyl groups, lower carboxyalkyl groups, aryl groups and aralkyl groups; $Q^{1a}$ is —$(CH_2)_m$— (wherein m is an integer of from 1 to 6) or —$(CH_2)_n$—$W^{1a}$—$(CH_2)_p$— (wherein $W^{1a}$ is an oxygen atom, a sulfur atom, a vinylene group or an ethynylene group; each of n and p which may be the same or different is an integer of from 0 to 3); $R^{1a}$ is a hydrogen atom, a halogen atom, a hydroxyl group, a lower alkyl group, a lower alkoxy group or an aryl or aromatic heterocyclic group which may have substituents selected from the group consisting of halogen atoms, lower alkyl groups and lower alkoxy groups; each of $R^{2a}$, $R^{7a}$ and $R^{8a}$ which may be the same or different is a hydrogen atom, a halogen atom, a hydroxyl group, a lower alkyl group or a lower alkoxy group; each of $R^{3a}$ and $R^{4a}$ which may be the same or different is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalklyl group or a lower alkoxy group; $R^{5a}$ is a lower alkyl group; and $R^{6a}$ is a hydrogen atom or a lower alkyl group, and wherein the agent which decreases farnesyl pyrophosphate in vivo is lovastatin, simvastatin, pravastatin or fluvastatin.

10. The antitumor or anti-AIDS composition according to claim 9, wherein the agent which decreases farnesyl pyrophosphate is simvastatin.

11. A method of suppressing the function of the Ras oncoprotein in a patient in need thereof, comprising administering to said patient effective amounts of a composition containing a protein-farnesyltransferase inhibitor and an agent which decreases farnesyl pyrophosphate in vivo as active ingredients.

12. The method according to claim 11, wherein the agent which decreases farnesyl pyrophosphate in vivo is a farnesyl pyrophosphate biosynthesis inhibitor.

13. The method according to claim 12, wherein the farnesyl pyrophosphate biosynthesis inhibitor is a hydroxymethylglutaryl CoA reductase inhibitor.

14. The method according to claim 13, wherein the hydroxymethylglutaryl CoA reductase inhibitor is lovastatin, simvastatin, pravastatin or fluvastatin.

15. The method according to claim 11, wherein the protein-farnesyltransferase inhibitor is a competitive inhibitor which competes with farnesyl pyrophosphate.

16. The method according to claim 11, wherein the protein-farnesyltransferase inhibitor is a compound represented by general formula or a pharmaceutically acceptable salt or ester thereof:

[I-a]

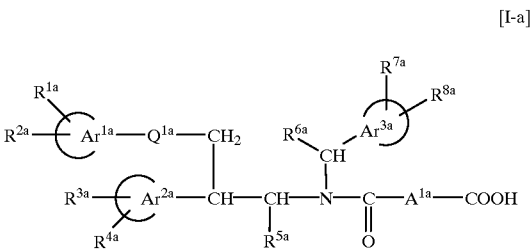

wherein each of

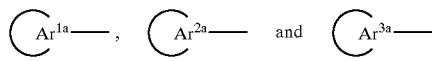

which may be the same or different is an aryl group or an aromatic heterocyclic group; $A^{1a}$ is a saturated or unsaturated aliphatic $C_{2-8}$ hydrocarbon group which may have substituents selected from the group consisting of lower alkyl groups, hydroxyl groups, lower hydroxyalkyl groups, lower alkoxy groups, carboxyl groups, lower carboxyalkyl groups, aryl groups and aralkyl groups; $Q^{1a}$ is —$(CH_2)_m$— (wherein m is an integer of from 1 to 6) or —$(CH_2)_n$—$W^{1a}$—$(CH_2)_p$— (wherein $W^{1a}$ is an oxygen atom, a sulfur atom, a vinylene group or an ethynylene group; each of n and p which may be the same or different is an integer of from 0 to 3); $R^{1a}$ is a hydrogen atom, a halogen atom, a hydroxyl group, a lower alkyl group, a lower alkoxy group or an aryl or aromatic heterocyclic group which may have substituents selected from the group consisting of halogen atoms, lower alkyl groups and lower alkoxy groups; each of $R^{2a}$, $R^{7a}$ and $R^{8a}$ which may be the same or different is a hydrogen atom, a halogen atom, a hydroxyl group, a lower alkyl group or a lower alkoxy group; each of $R^{3a}$ and $R^{4a}$ which may be the same or different is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^{5a}$ is a lower alkyl group; and $R^{6a}$ is a hydrogen atom or a lower alkyl group.

17. The method according to claim 11, wherein the protein-farnesyltransferase inhibitor is a compound represented by general formula or a pharmaceutically acceptable salt or ester thereof:

[1-b]

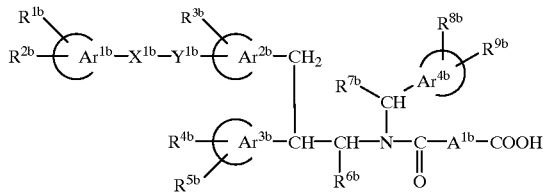

wherein each of

which may be the same or different is an aryl group or an aromatic heterocyclic group; $A^{1b}$ is a saturated or unsaturated aliphatic $C_{2-8}$ hydrocarbon group which may have substituents selected from the group consisting of lower alkyl groups, hydroxyl groups, lower hydroxyalkyl groups, lower alkoxy groups, carboxyl groups, lower carboxyalkyl groups, aryl groups and aralkyl groups; each of $X^{1b}$ and $Y^{1b}$ which may be the same or different is an oxygen atom, a sulfur atom, a carbonyl group, $-CHR^{10b}-$ (wherein $R^{10b}$ is a hydrogen atom or a lower alkyl group) or $-NR^{11b}-$ (wherein $R^{11b}$ is a hydrogen atom or a lower alkyl group), or $X^{1b}$ and $Y^{1b}$ together represent a vinylene group or an ethynylene group; each of $R^{1b}$, $R^{2b}$, $R^{3b}$, $R^{8b}$ and $R^{9b}$ which may be the same or different is a hydrogen atom, a halogen atom, a hydroxyl group, a lower alkyl group or a lower alkoxy group; each of $R^{4b}$ and $R^{5b}$ which may be the same or different is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^{6b}$ is a lower alkyl group; and $R^{7b}$ is a hydrogen atom or a lower alkyl group, provided that when either $X^{1b}$ or $Y^{1b}$ is an oxygen atom, a sulfur atom or $-NR^{11b}-$ (wherein $R^{11b}$ is the same as defined above), the other is a carbonyl group or $-CHR^{10b}-$ (wherein $R^{10b}$ is the same as defined above).

18. The method according to claim 11, wherein the weight ratio of the protein-farnesyltransferase inhibitor and the agent which decreases farnesyl pyrophosphate in vivo is from 0.001:1 to 1000:1.

19. A method of suppressing the function of the Ras oncoprotein in a patient in need thereof, comprising administering to said patient effective amounts of a composition containing a protein-farnesyltransferase inhibitor and an agent which decreases farnesyl pyrophosphate in vivo as active ingredients, wherein the protein-farnesyltransferase inhibitor is a compound represented by general formula or a pharmaceutically acceptable salt or ester thereof:

[I-a]

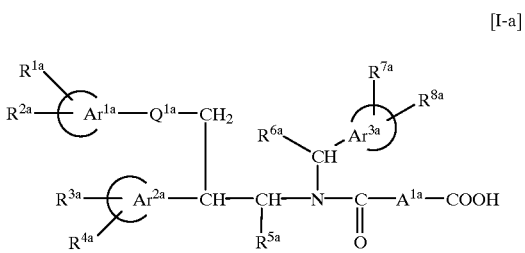

wherein each of

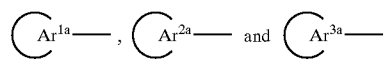

which may be the same or different is an aryl group or an aromatic heterocyclic group; $A^{1a}$ is a saturated or unsaturated aliphatic $C_{2-8}$ hydrocarbon group which may have substituents selected from the group consisting of lower alkyl groups, hydroxyl groups, lower hydroxyalkyl groups, lower alkoxy groups, carboxyl groups, lower carboxyalkyl groups, aryl groups and aralkyl groups; $Q^{1a}$ is $-(CH_2)_m-$ (wherein m is an integer of from 1 to 6) or $-(CH_2)_n-W^{1a}-(CH_2)_p-$ (wherein $W^{1a}$ is an oxygen atom, a sulfur atom, a vinylene group or an ethynylene group; each of n and p which may be the same or different is an integer of from 0 to 3); $R^{1a}$ is a hydrogen atom, a halogen atom, a hydroxyl group, a lower alkyl group, a lower alkoxy group or an aryl or aromatic heterocyclic group which may have substituents selected from the group consisting of halogen atoms, lower alkyl groups and lower alkoxy groups; each of $R^{2a}$, $R^{7a}$ and $R^{8a}$ which may be the same or different is a hydrogen atom, a halogen atom, a hydroxyl group, a lower alkyl group or a lower alkoxy group; each of $R^{3a}$ and $R^{4a}$ which may be the same or different is a hydrogen atom, a halogen atom, a hydroxyl group, an amino group, a nitro group, a cyano group, a carboxyl group, a lower alkoxycarbonyl group, a carbamoyl group, a lower alkylcarbamoyl group, a lower alkyl group, a lower hydroxyalkyl group, a lower fluoroalkyl group or a lower alkoxy group; $R^{5a}$ is a lower alkyl group; and $R^{6a}$ is a hydrogen atom or a lower alkyl group, and wherein the agent which decrease farnesyl pyrophosphate in vivo is lovastatin, simvastatin, pravastatin or fluvastatin.

20. The method according to claim 19, wherein the agent which decreases farnesyl pyrophosphate is simvastatin.

* * * * *